(12) United States Patent
Thomas et al.

(10) Patent No.: US 9,725,250 B2
(45) Date of Patent: *Aug. 8, 2017

(54) METHODS FOR HANDLING TUBULARS USEFUL DURING CLEANING AND INSPECTION OPERATIONS

(71) Applicant: Thomas Engineering Solutions & Consulting, LLC, New Iberia, LA (US)

(72) Inventors: William C. Thomas, Lafayette, LA (US); William J. Thomas, III, New Iberia, LA (US); Perry J. DeCuir, Jr., Rochester Hills, MI (US)

(73) Assignee: Thomas Engineering Solutions & Consulting, LLC, New Iberia, LA (US)

( * ) Notice: Subject to any disclaimer, the term of this patent is extended or adjusted under 35 U.S.C. 154(b) by 317 days.

This patent is subject to a terminal disclaimer.

(21) Appl. No.: 14/041,085

(22) Filed: Sep. 30, 2013

(65) Prior Publication Data

US 2014/0093347 A1    Apr. 3, 2014

Related U.S. Application Data

(60) Provisional application No. 61/707,780, filed on Sep. 28, 2012.

(51) Int. Cl.
*B65G 47/14* (2006.01)
*B08B 9/02* (2006.01)
(Continued)

(52) U.S. Cl.
CPC ............... *B65G 47/14* (2013.01); *B08B 9/02* (2013.01); *B08B 9/023* (2013.01); *B08B 9/0321* (2013.01);
(Continued)

(58) Field of Classification Search
CPC . E21B 19/14; E21B 19/22; B08B 9/02; B08B 9/043; B08B 9/0321; B65G 47/14; B65G 47/34
(Continued)

(56) References Cited

U.S. PATENT DOCUMENTS 1,927,847 A    9/1933    Resser
2,034,451 A    3/1936    Tripp
(Continued)

OTHER PUBLICATIONS

DeCuir, Perry J., "Optimizing Hydraulic Presses Using Data Acquisition Systems", proposed IFPE Paper, actual publication date unknown but prior to Feb. 1, 2012.

*Primary Examiner* — Michael McCullough
*Assistant Examiner* — Lynn Schwenning
(74) *Attorney, Agent, or Firm* — Zeman-Mullen & Ford, LLC

(57) ABSTRACT

Methods are disclosed for handling cylindrical tubulars in a process that, in preferred embodiments, also performs cleaning, inspection and other operations on the tubular. The tubular is held stationary while it is rotated. During rotation of the tubular, internal and external cleaning systems, and data acquisition systems, pass up and down the length of the rotating tubular. In preferred embodiments, a first tubular is loaded onto the handling machine, whereupon it is indexed and then rotated. Cleaning, inspection and other operations may be performed during rotation. Once operations are complete, the handling system ejects the first tubular while queuing up a second tubular to be loaded.

17 Claims, 18 Drawing Sheets

(51) Int. Cl.
    *B23Q 7/04*     (2006.01)
    *B23Q 7/00*     (2006.01)
    *B23Q 1/76*     (2006.01)
    *E21B 19/14*     (2006.01)
    *B08B 9/032*     (2006.01)
    *B08B 9/043*     (2006.01)
    *G01N 33/00*     (2006.01)
    *B65G 47/34*     (2006.01)
    *B08B 9/023*     (2006.01)
    *E21B 37/00*     (2006.01)
    *E21B 19/22*     (2006.01)
    *G01M 99/00*     (2011.01)

(52) U.S. Cl.
    CPC ............... *B08B 9/043* (2013.01); *B23Q 1/76* (2013.01); *B23Q 7/003* (2013.01); *B23Q 7/042* (2013.01); *B65G 47/34* (2013.01); *E21B 19/14* (2013.01); *E21B 19/22* (2013.01); *E21B 37/00* (2013.01); *G01N 33/00* (2013.01); *G01M 99/00* (2013.01); *Y10T 74/2186* (2015.01); *Y10T 82/2514* (2015.01); *Y10T 408/381* (2015.01)

(58) Field of Classification Search
    USPC ......... 414/745.7, 745.1, 745.4, 745.9, 746.1, 414/746.3, 746.5, 806, 910, 911
    See application file for complete search history.

(56) References Cited

U.S. PATENT DOCUMENTS

| | | |
|---|---|---|
| 2,114,974 A | 4/1938 | Camerota |
| 2,500,204 A | 3/1950 | Ronay |
| 2,519,837 A | 8/1950 | Lampard |
| 2,585,325 A | 2/1952 | Imshaug |
| 2,623,570 A | 12/1952 | Resser et al. |
| 2,873,716 A | 2/1959 | Daniel |
| 2,925,166 A | 2/1960 | Sawdey |
| 3,315,822 A | 4/1967 | Wilson |
| 3,458,055 A | 7/1969 | Council |
| 3,571,981 A | 3/1971 | Schaller et al. |
| 3,726,463 A | 4/1973 | Hoffmann et al. |
| 3,985,221 A | 10/1976 | Lueders |
| 4,166,301 A * | 9/1979 | Smith ................ B08B 9/027 15/104.04 |
| 4,205,407 A * | 6/1980 | King ................ B08B 9/023 15/179 |
| 4,417,363 A | 11/1983 | Lee, Jr. |
| 4,465,422 A | 8/1984 | Blust et al. |
| 4,533,055 A | 8/1985 | Haney |
| 5,030,911 A | 7/1991 | Lam |
| 5,060,423 A | 10/1991 | Klotz |
| 5,673,843 A | 10/1997 | Gainey |
| 5,969,255 A * | 10/1999 | McLean ................ B21O 51/00 73/622 |
| 6,149,376 A | 11/2000 | Peting |
| 6,290,573 B1 | 9/2001 | Suzuki |
| 6,389,941 B1 | 5/2002 | Michler |
| 6,622,561 B2 * | 9/2003 | Lam ................ G01N 29/0609 73/620 |
| 7,007,729 B1 | 3/2006 | Landers |
| 7,263,887 B2 | 9/2007 | Sfeir et al. |
| 8,113,762 B2 | 2/2012 | Belik |
| 9,248,976 B2 | 2/2016 | Thomas et al. |
| 2008/0021662 A1 | 1/2008 | Hinn |
| 2009/0196711 A1 | 8/2009 | Gerber et al. |
| 2009/0217954 A1* | 9/2009 | Hall ................ G01B 11/245 134/115 R |
| 2011/0074332 A1 | 3/2011 | Baker |

\* cited by examiner

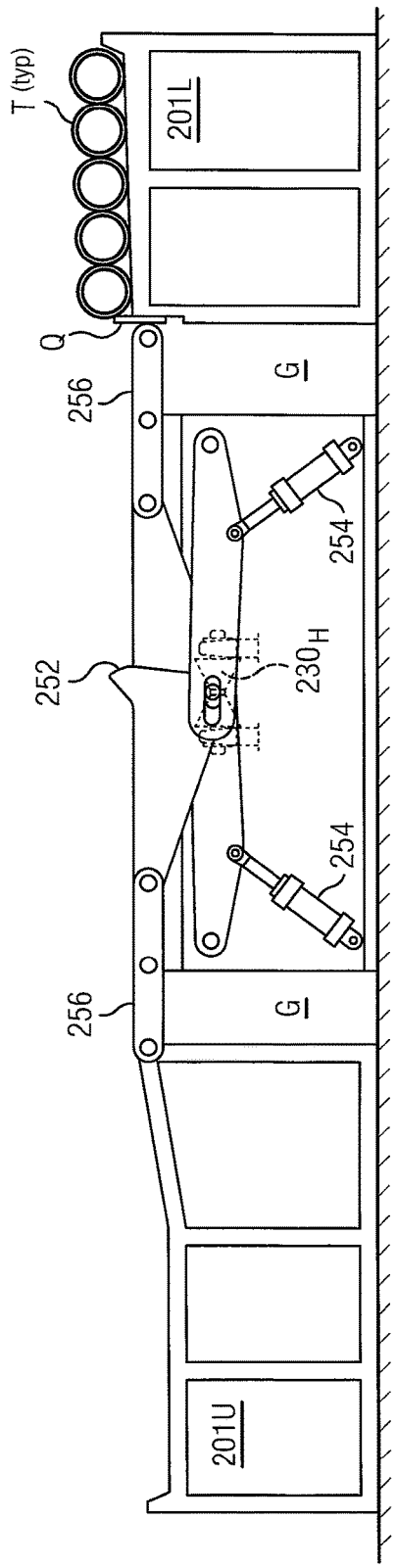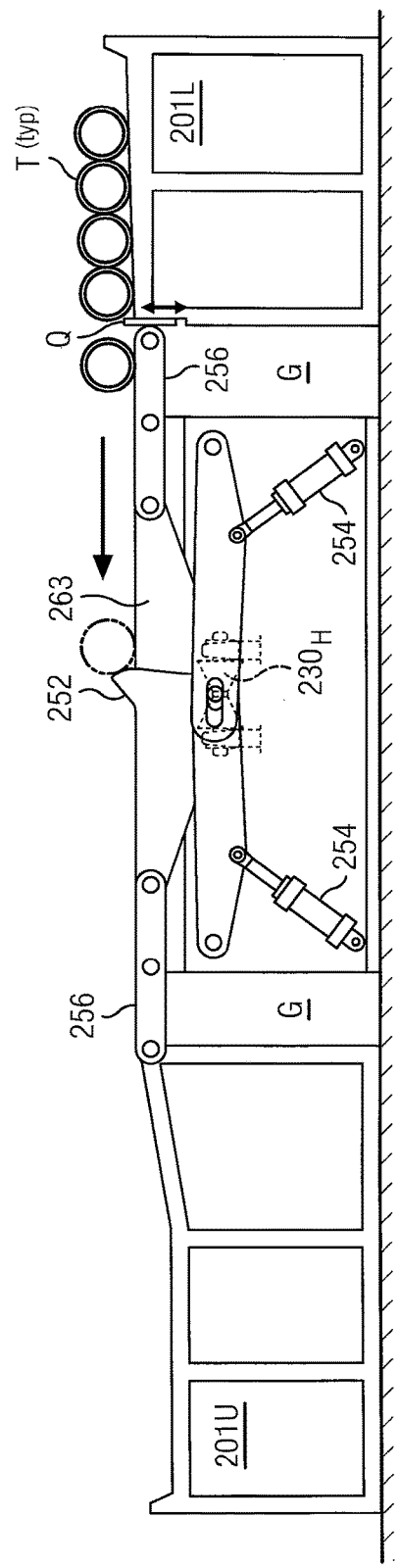
FIG. 15A
FIG. 15B

METHODS FOR HANDLING TUBULARS USEFUL DURING CLEANING AND INSPECTION OPERATIONS

RELATED APPLICATIONS

This application claims the benefit of, and priority to, commonly-assigned U.S. Provisional Application Ser. No. 61/707,780, filed Sep. 28, 2012.

FIELD OF THE INVENTION

This disclosure is directed generally to technology for handling tubulars deployed in the oil and gas exploration field, such as drill pipe, workstring tubulars, and production tubulars, and more specifically to handling during operations such as cleaning and inspection of the tubulars.

BACKGROUND OF THE INVENTION

Throughout this disclosure, the term "Scorpion" or "Scorpion System" refers generally to the disclosed Thomas Services Scorpion brand proprietary tubular management system as a whole.

In conventional tubular cleaning operations, the cleaning apparatus is typically stationary, while the tubular is drawn longitudinally past the cleaning apparatus. The tubular is rotated at a relatively slow speed (in the range of 50 rpm, typically) while stationary, spring-loaded air motors drive spinning wire brushes and cutter heads on the inside diameter of the tubular as it is drawn past, via skewed drive rollers. These air brushes are colloquially called "cutters" although they perform abrasive cleaning operations on the internal surface of the tubular. Internal tubular cleaning operations typically also include hydroblasting in the prior art, although this is conventionally understood to be supplemental to the wire brush cleaning described above, rather than a primary cleaning process in and of itself. Typically this conventional hydroblasting is a low pressure water or steam pressure wash at pressures ranging from about 2,500 psi to 3,500 psi.

Good examples of conventional tubular cleaning apparatus are marketed by Knight Manufacturing, Inc. (formerly Hub City Iron Works, Inc.) of Lafayette, La. These products can be viewed on Knight's website.

One drawback of conventional tubular cleaning apparatus is that, with the cleaning apparatus stationary and the tubular drawn longitudinally across, the apparatus requires a large building. Range 3 drilling pipe is typically 40-47 feet long per joint, which means that in order to clean range 3 pipe, the building needs to be at least approximately 120 feet long

SUMMARY OF THE INVENTION

Aspects of the Scorpion System disclosed and claimed in this disclosure address some of the above-described drawbacks of the prior art. In preferred embodiments, the Scorpion System rotates the tubular to be cleaned (hereafter, also called the "Work" in this disclosure) while keeping the Work stationary with respect to the cleaning apparatus. The Scorpion then moves the cleaning apparatus up and down the length of the Work while the Work rotates.

In currently preferred embodiments, the Work is typically rotated at speeds in a range of about 400-500 rpm, and potentially up to 1,750 rpm under certain criteria. By contrast, the Work may also be rotated as slowly as 0.01 rpm in such currently preferred embodiments, in order to facilitate high resolution local cleaning, inspection or data gathering/analysis. However, nothing in this disclosure should be interpreted to limit the Scorpion System to any particular rotational speed of the Work. Currently preferred embodiments of the Scorpion System further draw the cleaning apparatus up and down the length of the Work at speeds within a range of about 0.5 to 5.0 linear feet per second ("fps"), depending on the selected corresponding rotational speed for the Work. Again, nothing in this disclosure should be interpreted to limit the Scorpion System to any particular speed at which the cleaning apparatus may move up or down the length of the Work.

The Scorpion System provides a multi-lance injector assembly (MLI) to clean and inspect the internal surface of the Work. Tools, sensors and other equipment are provided on the end of one or more lances. The lances may be injected in and out of the inside of the Work as the Work rotates. Currently preferred embodiments of the MLI are disclosed in commonly-assigned, co-pending U.S. patent application Ser. No. 13/832,340.

The Scorpion System further provides an outer delivery system (ODS) to clean and inspect the external surface of the Work. Tools, sensors and other equipment are provided on a buggy. The buggy may be moved up and down the exterior of the Work as the Work rotates. Currently preferred embodiments of the ODS are disclosed in commonly-assigned, co-pending U.S. patent application Ser. No. 14/040,650.

The Scorpion System further provides a pipe handling system (PHS) to handle tubulars on a continuous basis throughout the cleaning and inspection operations. This disclosure is directed to the PHS. The basic functions performed by the PHS are: (1) to bring a new tubular into the Scorpion System; (2) to lower the tubular onto an indexer, which then indexes the tubular into a desired longitudinal position; (3) to lower the indexed tubular into drive and pressure rollers, which then rotate the tubular as desired while cleaning and inspection operations are performed; (4) to raise the cleaned and/or inspected tubular out of the drive and pressure rollers and eject the tubular from the Scorpion System. FIG. 1 illustrates this basic process in a continuous routine. FIG. 1 is described in more detail further on in this disclosure.

Note that although disclosed herein as part of the Scorpion System, the disclosed PHS could be used in many tubular moving operations. It is not limited to loading up a tubular cleaning system. It is also not limited to pipe and tubulars. It is also applicable to moving rods or other solid cylindrical pieces.

It is therefore a technical advantage of the disclosed PHS to save footprint by enabling cleaning, inspection or other operations to be performed on a rotating tubular that is otherwise held stationary in longitudinal and lateral positions.

A further technical advantage of the disclosed PHS is to optimize processing time by handling tubulars of the same diameter and length in cycles repeating in automatic or semi-automatic modes.

A further technical advantage of the disclosed PHS is to have the versatility to process tubulars in a wide variety of diameters and lengths, and to enable cleaning, inspection or other operations in a wide variety of rotational speeds, changeable on the fly per user selection.

The foregoing has outlined rather broadly some of the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIGS. 15A through 15G are a series of "freeze frame" illustrations depicting the general operation of pods 220.

DETAILED DESCRIPTION

Figure 1:
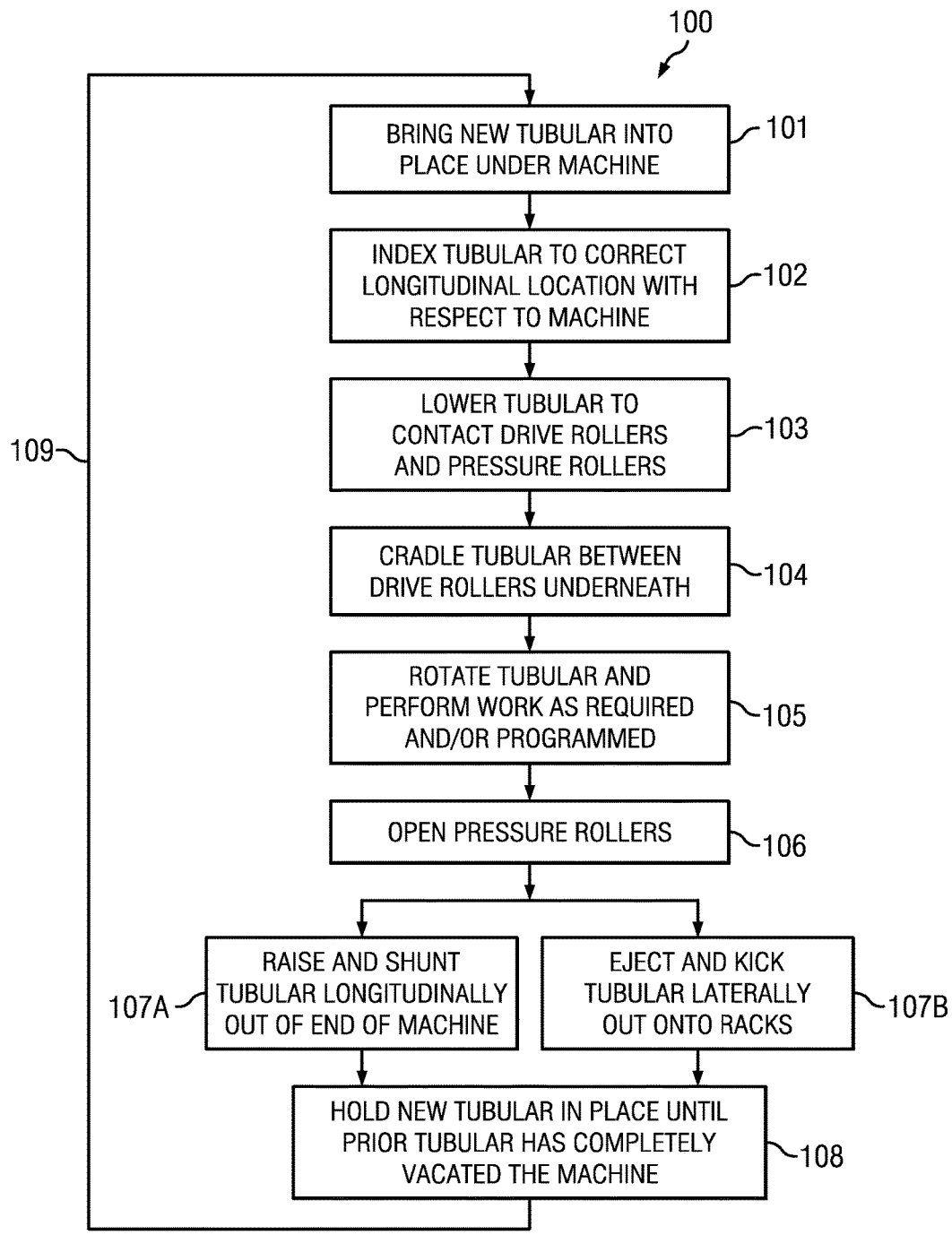
FIG. 1 is a flow chart illustrating the basic functions of the disclosed PHS in a continuous routine.

FIG. 1 is a flow chart describing a currently preferred PHS method 100. Blocks 101 through 108 represent steps of the method in summary form, and as described in greater detail in the written disclosure immediately below. Block 109 on FIG. 1 illustrates PHS method 100 in the example of fully automatic mode, where the steps of PHS method 100 may be repeated on the Scorpion System. In such fully automatic mode, tubular handling cycles may cooperate with cleaning, data acquisition and other operational cycles that are described in other commonly-assigned U.S. patent disclosures, including those to which priority is claimed herein, and those referenced above in the "Summary" section.

Block 101 on FIG. 1 refers to loading a length of pipe or other tubular onto the PHS. As will be described further on with reference to additional Figures, currently preferred embodiments of the PHS enable this step by allowing the tubular to roll off rack storage onto a scissors mechanism in the "up" position. A nub located on one of the arms of the scissors mechanism brings the tubular to rest in a desired location generally above the fulcrum of the scissors mechanism. The scissors mechanism is then moved to the "down" position, thereby lowering the tubular. The tubular comes to rest on the index rollers of an indexing machine in the "up' position.

Block 102 on FIG. 1 refers to indexing, a term used in this disclosure to mean positioning the tubular at a desired longitudinal location with respect to the machine. As will be described further on with reference to additional Figures, currently preferred embodiments of the PHS enable this step by rotating the index rollers. In currently preferred embodiments, precision indexing is highly desirable in order to facilitate the precision cleaning, inspection and data acquisition advantages offered by other aspects of the Scorpion System.

In other embodiments, however, and in other applications, precision indexing may be optional, although useful for irregular-sized or damaged tubulars. In such other embodiments that forego precision indexing, gravity indexing is nonetheless preferred to promote overall cycle time efficiency for sequential operations on a series of regularly-sized tubulars. An example of a gravity indexing deployment allows a tubular to roll or slide longitudinally onto, for example, a trestle with rollers and comes to rest on the trestle at a pre-positioned indexing stop. The tubular is then permitted to roll down the trestle into position for cleaning and/or other operations.

As noted above, precision indexing is highly desirable in preferred embodiments of the Scorpion System, as described in greater detail below with reference to additional Figures. However, in other applications, gravity indexing may be precise enough to identify where the tubular is set in order to start and stop exterior surface operations. Further, the Knuckle-Jointed Lancer (KJL) assemblies, as described with reference to the Multi-Lance Injector (MLI) assembly disclosed in commonly-assigned, co-pending U.S. patent application Ser. No. 13/832,340, may be stiff enough in preferred embodiments to accommodate small variations in longitudinal position of the tubular (that might occur as a result of gravity indexing) without loss in ability to extend and retract into and out of the tubular during internal surface operations.

Returning now to a discussion of precision indexing, and with further reference to block 102 on FIG. 1, once the tubular has been indexed to a desired longitudinal position by the index rollers, the indexing machine is moved from its "up" position to its "down" position, thereby lowering the tubular. The tubular comes to rest on drive rollers in the rolling machine.

Blocks 103, 104 and 105 on FIG. 1 refer to rotating the now-indexed tubular at selectable speeds, up to high speed, in a controlled way. As will be described further on with reference to additional Figures, currently preferred embodiments of the PHS enable these steps by rotating the drive rollers on which the tubular now rests. More specifically, pairs of drive rollers "cradle" the tubular from below. Counterpart pairs of pressure rollers are then engaged to contact the tubular from above, thereby retaining the tubular on the drive rollers. The pairs of drive rollers and counterpart pairs of pressure rollers may be pre-set at user-selected distances apart to accommodate different diameters of tubular. Preferred embodiments favor setting drive rollers such that they cradle the tubular at points of contact at azimuths of about 135 degrees and 225 degrees (where the tubular's cross-section is visualized with zero degrees pointing vertically upwards). Pressure rollers in such embodiments will contact the tubular at azimuths of about 45 degrees and 315 degrees. These azimuths are chosen in a preferred embodiment for best effectiveness in controlling harmonic vibrations arising in the tubular during rotation or acceleration. It will be nonetheless understood that such cradling points are exemplary only, and that nothing herein shall be construed to limit the Scorpion System in this regard. Pairs of drive rollers and counterpart pairs of pressure rollers are configured to allow a passing ODS (with its associated shrouded cleaning media jets, brushes, sensors, etc.) unimpeded and continuous access to the top portion of the tubular (between pressure rollers) along the entire length of the tubular as the tubular rotates. See commonly-assigned, co-pending U.S. patent application Ser. No. 14/040,650 for further disclosure on the ODS referenced immediately above.

The drive and pressure rollers combine to offer good vibration control during high speed rotation. Unlike other conventional arrangements where the tubular might be made up via screwed connections and then rotated from the inside, as if it were on a lathe, the PHS system achieves high speed rotation of tubulars in a "free-rolling" (i.e. torsionally unrestrained) environment.

Blocks 106, 107A and 107B on FIG. 1 refer to unloading the tubular once cleaning, inspection or other operations are complete. Blocks 107A and 107B describe different embodiments of the method. In presently preferred embodiments of the Scorpion System, the method according to block 107B is more desirable. As will be described further on with reference to additional Figures, currently preferred embodiments of the PHS enable these steps by generally reversing the process described above with reference to blocks 101, 102 and 103. Once the rotating tubular has been brought to a standstill, the pressure rollers are opened (see block 106 on FIG. 1), and the indexing machine is moved to its "up" position. As the indexing machine rises, it contacts the tubular with the index rollers and picks the tubular up off the drive rollers. The index rollers may then shunt the tubular out of the PHS longitudinally (see block 107A on FIG. 1).

More preferably, once the index machine has lifted the tubular off the drive rollers, the scissors mechanism may then be moved to its "up" position and take the tubular off the index rollers. Alternatively the scissor mechanism may be moved to its "up" position as soon as the pressure rollers are opened, and take the tubular directly off the drive rollers. As the scissors mechanism approaches its "up" position, the nub on one of its arms contacts the tubular. Further travel by the scissors mechanism to the "up" position causes the nub to push (eject) the tubular laterally onto unload-side rack storage on the opposite side from where the tubular came into the PHS (see block 107B on FIG. 1).

Once the tubular has vacated the PHS and into unload-side rack storage, a stop on the load-side rack storage then releases the next tubular onto the PHS, and the pipe handling cycle starts over (see block 108 and arrow 109 on FIG. 1). In this way, the scissors mechanism on the PHS eliminates the need for two separate sets of apparatus, one to load tubulars, and one to unload.

Tubulars in the queue to be loaded onto the PHS are advantageously held in a specially shaped unload-side racking system, including a racking mechanism and temporary storage. Tubulars in the unload-side racking system are stacked and positioned in a predetermined location so that they may be taken one-by-one off the racking system and placed ready for further processing.

It will be appreciated that deployments of the PHS can be either portable or in a building. The deployment requires a stable base, advantageously enabled by a steel structure geometrically designed with a low center of gravity in order to resist overturning and shifting caused by heavy pipe impacts and other acceleration-force-momentum changes.

It is anticipated that with preferred embodiments of the PHS deployed on the Scorpion System, tubular cleaning operations may be conducted in at least 3 modes: manual, semi-automatic and fully automatic. In semi-automatic mode, there would be a manual load up and index of the tubular, and the disclosed apparatus would accomplish all programmed cleaning and inspection cycles without further manual interaction. In fully automatic mode, the apparatus may further execute sequential operations (load, index, clean, inspect and remove) for identical tubulars without the need for further manual interaction. As noted above, embodiments having capability for such automatically repeatable cycles of PHS are illustrated on FIG. 1 by line 109.

It will be further appreciated that in fully automatic mode, additional sensors and logic processing will be required to separate out the cycles for each tubular as it is loaded, indexed, cleaned, inspected and unloaded from the cleaning apparatus.

Referring to fully automatic mode in more detail, a system operator may advantageously pre-select process parameters such as tubular dimensions (e.g. length, outside diameter), rotational speed, or number of cleaning passes (inside and outside). The PHS will then take over control and clean a series of tubulars in accordance with the pre-selected parameters without further control interaction with the operator. During this automatic operation, the PHS will further advantageously adjust parameters such as rotational speed in accordance with real-time sensor readings of conditions such as a tubular's vibrational response to a particular pre-programmed rotational speed.

FIGS. 2 through 15G illustrate one exemplary embodiment (and on the Scorpion System, a currently preferred embodiment) of a PHS enabling the method described above with reference to FIG. 1. Parts and items appearing on more than one of FIGS. 2 through 15G have the same numeral.

Figure 2:
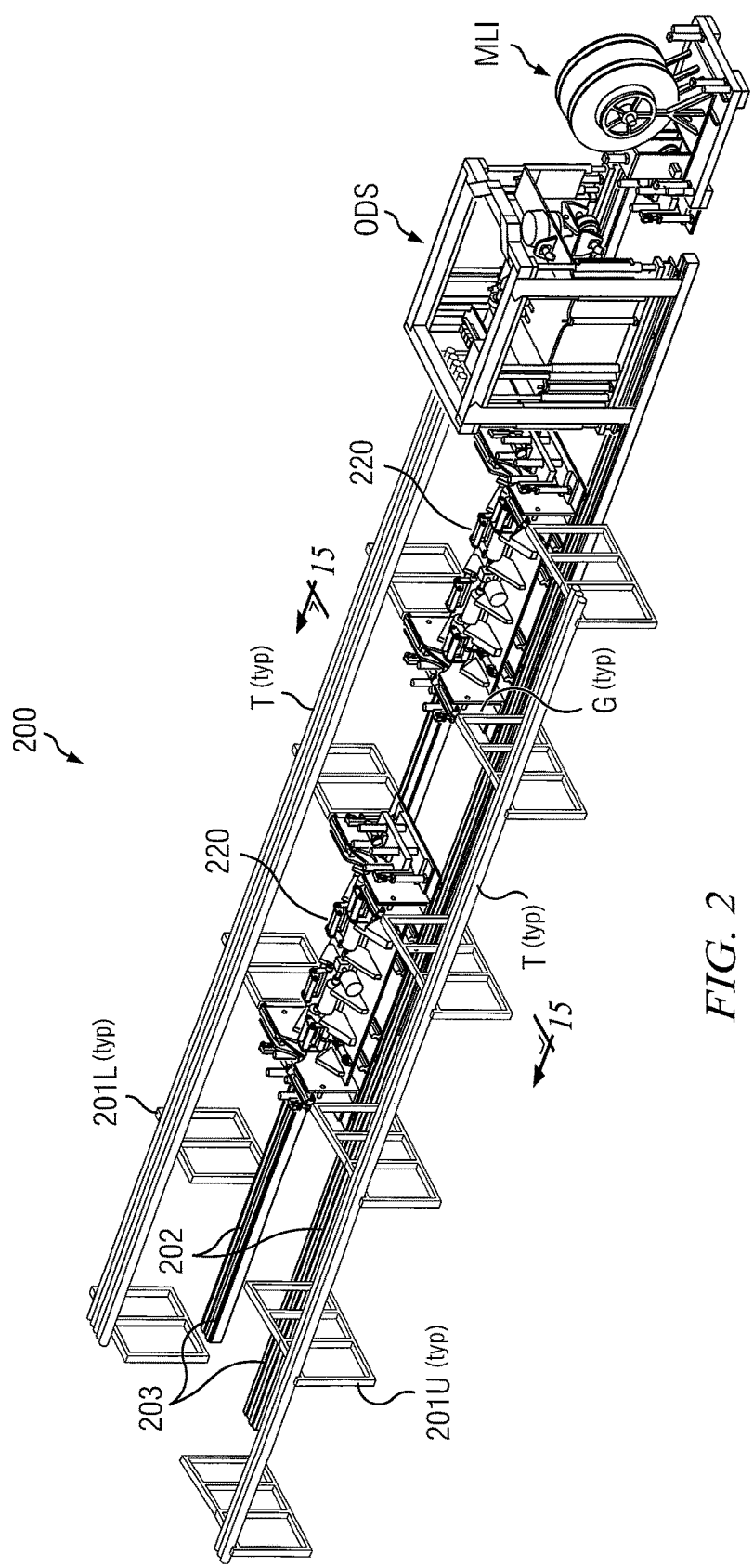
FIG. 2 is a general arrangement of an exemplary deployment of the Scorpion System, including PHS 200.

FIG. 2 is a general arrangement of an exemplary deployment of the Scorpion System, including PHS 200. FIG. 2 also shows Multi-Lance Injector (labeled "MLI" on FIG. 2), and Outer Delivery System (labeled "ODS" on FIG. 2), embodiments of which are disclosed in commonly assigned, co-pending U.S. patent application Ser. No. 14/040,650 (ODS) and Ser. No. 13/832,340 (MLI). Note that ODS on FIG. 2 is illustrated in its rest position, between MLI and PHS 200, at a location where it will not impede the operation of PHS 200.

PHS 200 on FIG. 2 will be understood to be serviced by a load-side rack including load-side trestles 201L, and an unload-side rack including unload-side trestles 201U. Pluralities of tubulars T are shown resting on load-side trestles 201L and unload-side trestles 201U. For purposes of illustration, it will be understood that standing at ODS, with one's back to MLI and looking down PHS 200, tubulars T on the right hand side are awaiting load up by PHS 200 in preparation for cleaning, inspection or other operations by ODS and MLI. Tubulars T on the left hand side have had such cleaning, inspection or other operations completed on them, and have been subsequently unloaded by PHS 200. It will be further appreciated that PHS is not limited to this orientation, and other embodiments may process tubulars in the opposite lateral direction.

PHS 200 on FIG. 2 comprises two pods 220. Pods 220 are described in more detail later on with reference to additional Figures. Pods 220 each comprise cooperating structure for receiving tubulars T from load-side trestles 201L, indexing the tubulars T, rotating the tubulars T during cleaning, inspection and other operations on tubulars T, and then ejecting the tubulars T onto unload-side trestles 201U when such cleaning, inspection and other operations are completed. Each pod 220 runs on pod rails 203, and is independently movable up and down PHS 200. It will be understood that the pods 220 may be individually pre-positioned along pod rails 203 to suit different lengths of tubulars T. Once the positions of pods 220 along pod rails 203 are selected and set for a given length of tubular T (or a series thereof having the same length), pods 220 may then be secured in those positions. The scope of this disclosure is not limited to any particular mechanism used to move pods 220 along pod rails 203. In some embodiments, pods 220 may be moved and secured manually. In other embodiments, pods may be moved and secured mechanically, such as via motor-driven sprockets or worm gears rotating in teethed rails.

Although FIG. 2 illustrates PHS 200 as having two (2) pods 220, it will be understood that PHS 200 is not limited in that regard. Other embodiments of PHS 200 may have any number of pods to properly support and handle the length of tubulars T being received. It will be also understood that other embodiments of PHS 200 may provide pods 220 in fixed positions, without pod rails 203, when the versatility to choose different positions for pods 220 is not needed.

Pods 220 are described in detail later on with reference to further Figures. However, it will be understood that in the embodiment of PHS 200 illustrated on FIG. 2, pods 220 are substantially identical in structure. Having substantially identical pods 220 facilitates combined and concurrent inter-cooperative control of pods 220 in handling a single tubular T. It will be appreciated that conflict in operations or control between different pods 220 on a single tubular T would likely be disadvantageous. However, nothing in this disclosure should be interpreted to limit PHS 200 to substantially identical pods 220. So long as the goal of combined and concurrent inter-cooperative control of pods 220 can be achieved to as not to cause conflict in operations, it is within the scope of this disclosure for PHS 200 to provide dissimilar pods 220.

FIG. 2 further illustrates ODS rails 202 running outside of pod rails 203, but inside of load-side trestles 201L and, unload-side trestles 201U. It will be understood with further reference to commonly-assigned co-pending U.S. patent application Ser. No. 14/040,650, ODS on FIG. 2 moves up and down ODS rails 202 to perform external cleaning and inspection operations on a tubular T while PHS 200 rotates tubular T. It will be seen from FIG. 2 that in an operating mode, there are gaps G provided between load-side trestles 201L and pods 220 (on the load side of pods 220), and unload-side trestles 201U and pods 220 (on the unload side of pods 220). Gaps G are selected to be wide enough, and ODS is designed to give sufficient clearance over pods 220, to allow ODS to travel unimpeded on ODS rails 202 over the entire length of a tubular T being held and rotated in pods 220. Gaps G are further wide enough to give ODS clearance from load-side trestles 201L and unload-side trestles 201U as ODS travels up and down ODS rails 202. Such clearance for ODS thus allows tools and sensors on ODS to operate on the entire length of a tubular T being held and rotated in pods 220.

Figure 3:
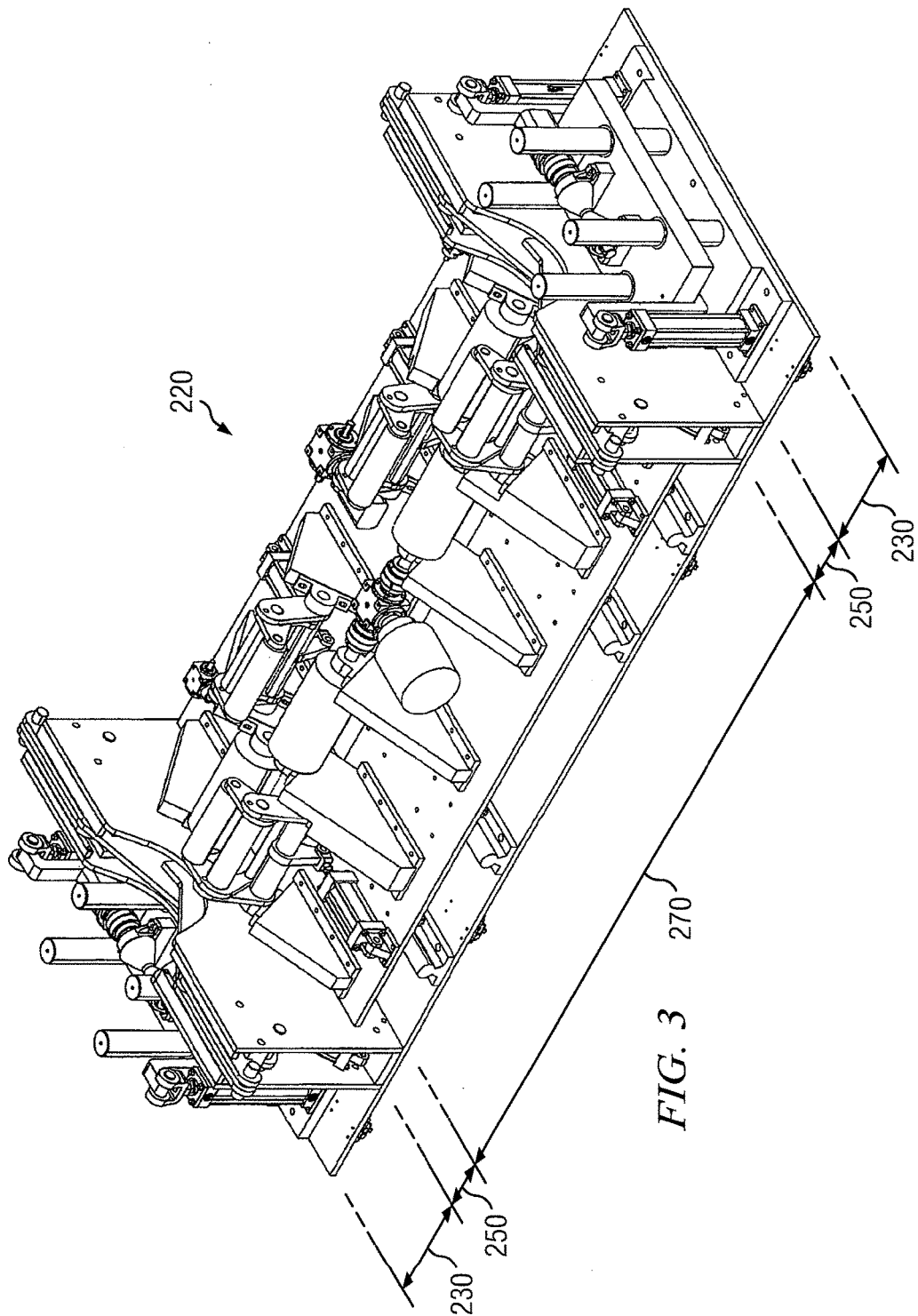
FIG. 3 illustrates a pod 220 in isolation.

FIG. 3 illustrates a pod 220 in isolation. As shown on FIG. 3, each pod 220 comprises three generally distinct components for handling tubulars: index machine 230, scissors mechanism 250 and rolling machine 270. Each of index machine 230, scissors mechanism 250 and roller machine 270 will be described in more detail, in isolation and with reference to additional Figures. As noted in earlier disclosure, however, the embodiment of PHS 200 illustrated on FIG. 2 provides pods 220 that are substantially identical in structure. Thus, in such embodiments, and with further reference to FIG. 3, the index machine 230 on one pod 220 is substantially identical to the index machine 230 on other pods 220. Index machines 230 may then easily cooperate operatively with index machines 230 on other pods 220. Likewise, scissor mechanism 250 on one pod 220 is substantially identical to the scissor mechanism 250 on other pods 220. Scissor mechanisms 250 may then easily cooperate operatively with scissor mechanisms 220 on other pods 220. Similarly, the rolling machine 270 on one pod 220 is substantially identical to the rolling machine 270 on other pods 220. Rolling machines 270 may then easily cooperate operatively with rolling machines 270 on other pods 220.

It will be further seen on FIG. 3 that each of index machine 230 and scissors mechanism 250 has two (2) separate, substantially identical cooperating halves. Rolling machine 270 is illustrated on FIG. 3 in one physical unit, although the unit comprises two (2) substantially identical, cooperating mirror-image halves on board. It will be appreciated from disclosure further below, with reference to later Figures, that the PHS generally disclosed herein is not limited to generally to embodiments of index machine 230, scissors mechanism 250 and roller machine 270 that two substantially identical halves on a pod 220. Other, non-identical combinations on a single pod 220, or across multiple pods 220, are within the scope of this disclosure, with or without cooperating halves. Further, other embodiments may provide pods 220 with any number of index machines 230, scissors mechanisms 250 or roller machines 270.

Figure 4:
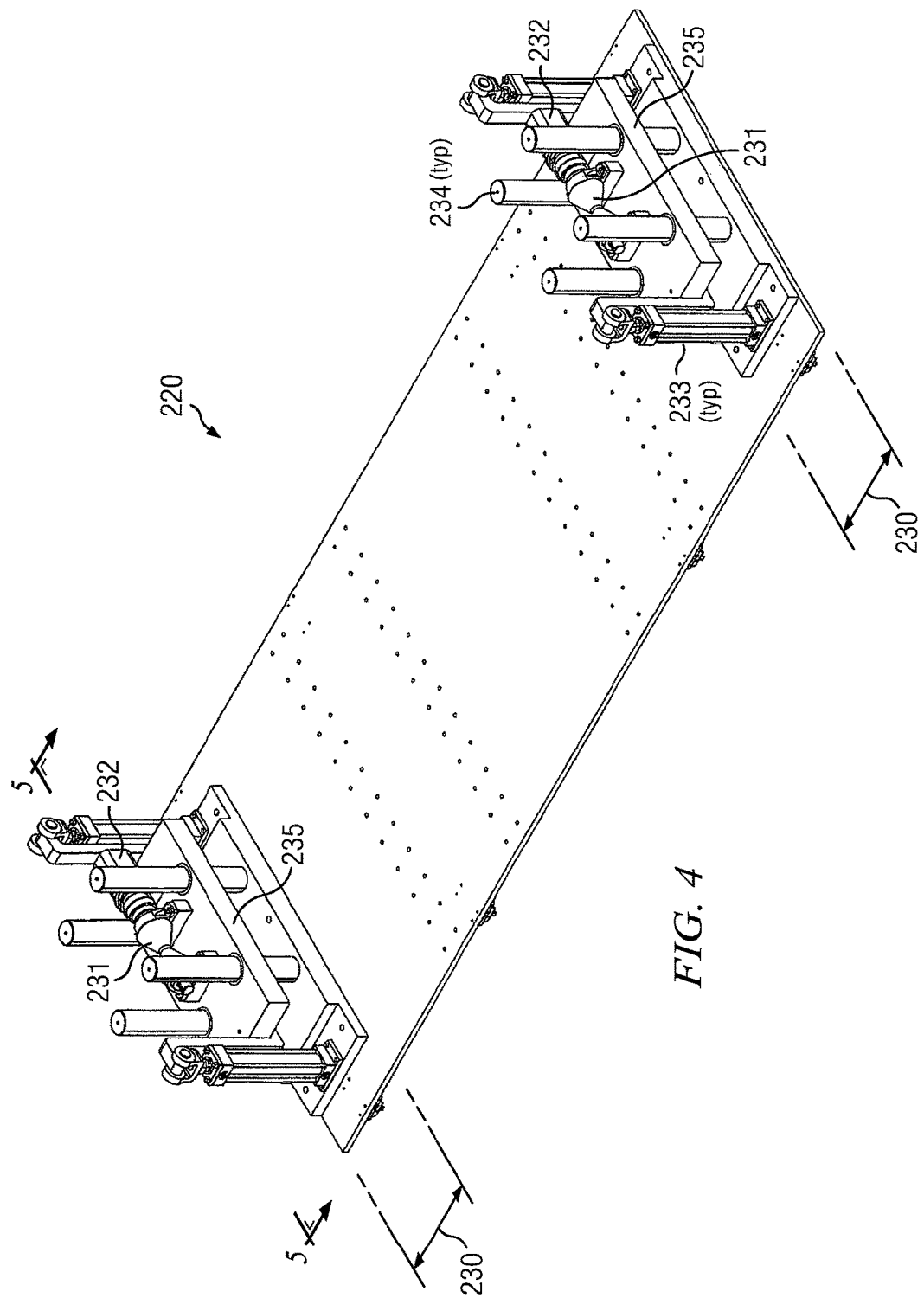
FIG. 4 is an illustration taken from FIG. 3, showing index machine 230 on pod 220 in isolation.

FIG. 4 is an illustration taken from FIG. 3, showing index machine 230 on pod 220 in isolation. Each half of index machine 230 provides index roller 231 driven by index roller motor 232. Index rollers 230 are fixed to index platform 235 on each half. Index pistons 233 are disposed to raise index platforms 235 up and down index guides 234. It will be thus appreciated that when a tubular is rested on index rollers 231, index roller motors 232 may be cooperatively actuated to displace the tubular longitudinally to a user-selected longitudinal position. Likewise index pistons 233 may be actuated cooperatively to raise and lower the tubular, resting on index rollers 231, to a user-selected elevation.

Figure 5:
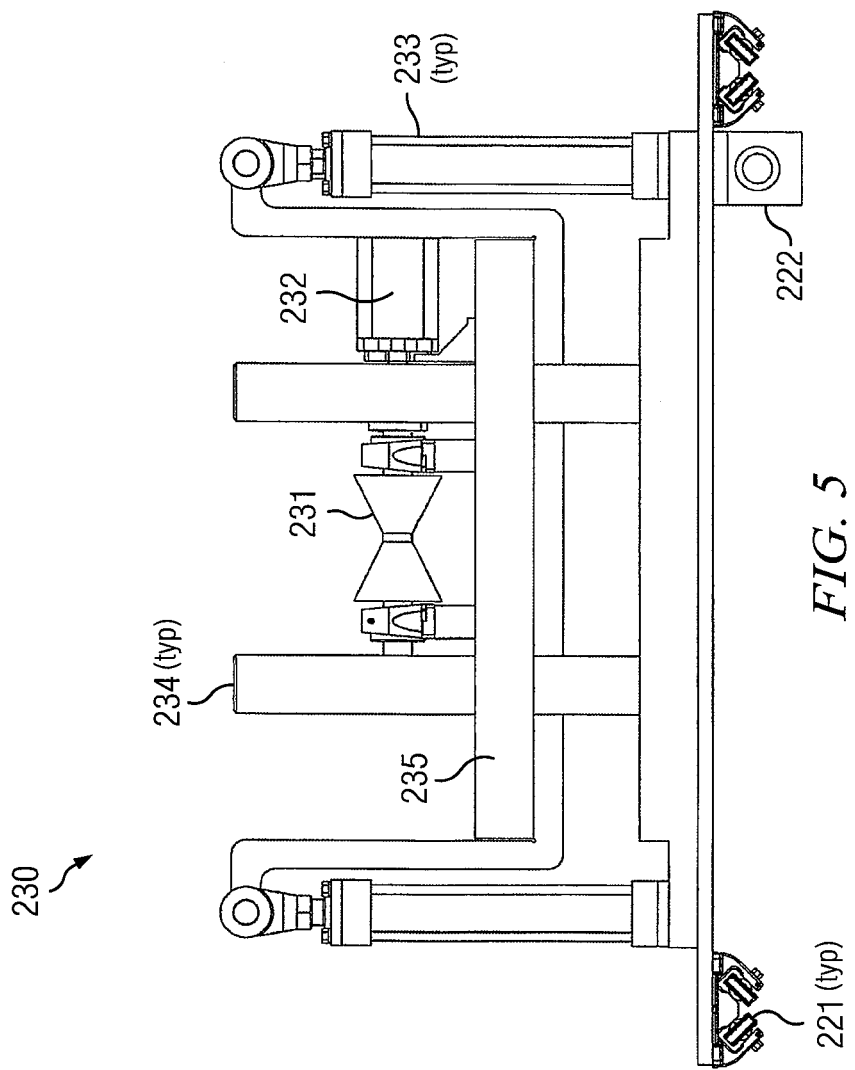
FIG. 5 is an elevation view of one half of index machine 230 as shown on FIG. 4.

FIG. 5 is an elevation view of one half of index machine 230 as shown on FIG. 4, and shows index roller 231, index roller motor, 232, index pistons 233, index guides 234 and index platform 235 in more detail. FIG. 5 also illustrate pod wheels 221 and pod stop 222. With further reference to FIG. 2, pod wheels run on pod rails 203, and pod stop 222 is used to provide a selectable physical stop (for safety, for example) for pod 220 moving up and down pod rails 203. Pod wheels 221 and pod stop 222 will be discussed further on in this disclosure with reference to additional Figures.

Figure 6:
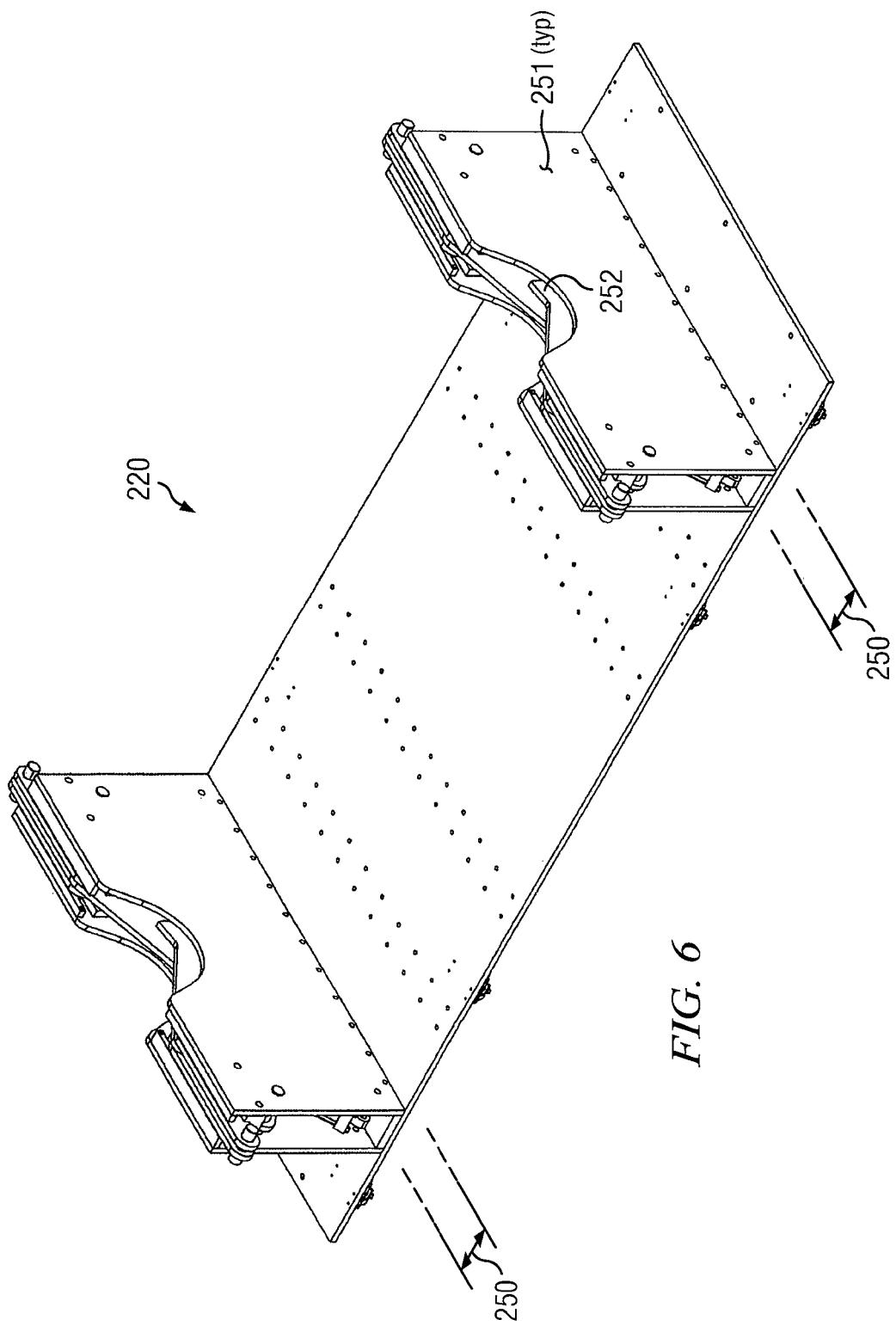
FIG. 6 is an illustration taken from FIG. 3, showing scissors mechanism 250 on pod 220 in isolation.

FIG. 6 is an illustration taken from FIG. 3, showing scissors mechanism 250 on pod 220 in isolation. Each half of scissors mechanism 250 on FIG. 3 provides identical structure for loading a tubular laterally onto pod 220, for ejecting the tubular laterally once work on the tubular is complete, and for receiving the next tubular laterally as the completed tubular leaves. The structure for loading, ejecting and receiving tubulars in each half of scissors mechanism 250 may thus cooperate operatively in one pod 220 (and across multiple pods 220) to handle the tubular. With further reference to FIG. 6, the structure for loading, ejecting and receiving tubulars is retained in each half of scissors mechanism 250 by scissors end plates 251. Such structure is thus not readily apparent on FIG. 6. However, two (2) of the features of scissors mechanism 250 that are visible on FIG. 6 are nub 252, and the fact that the scissors mechanism is illustrated on FIG. 6 in the "down" position. These features will be further described in detail below with reference to additional Figures.

Figure 7A:
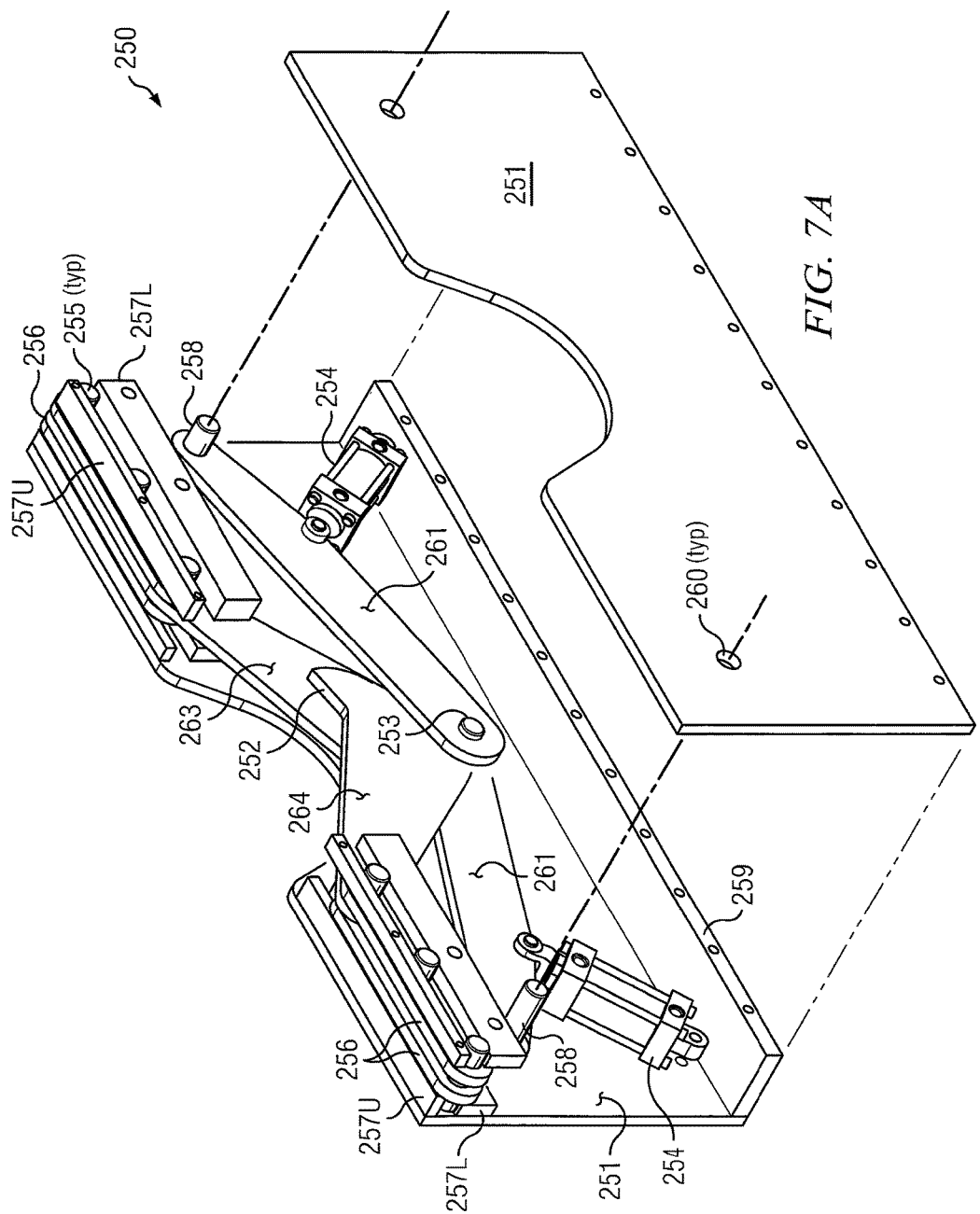
FIGS. 7A and 7B each illustrate one half of scissors mechanism 250 from FIG. 6, each in progressing stages of disassembly.
Figure 7B:
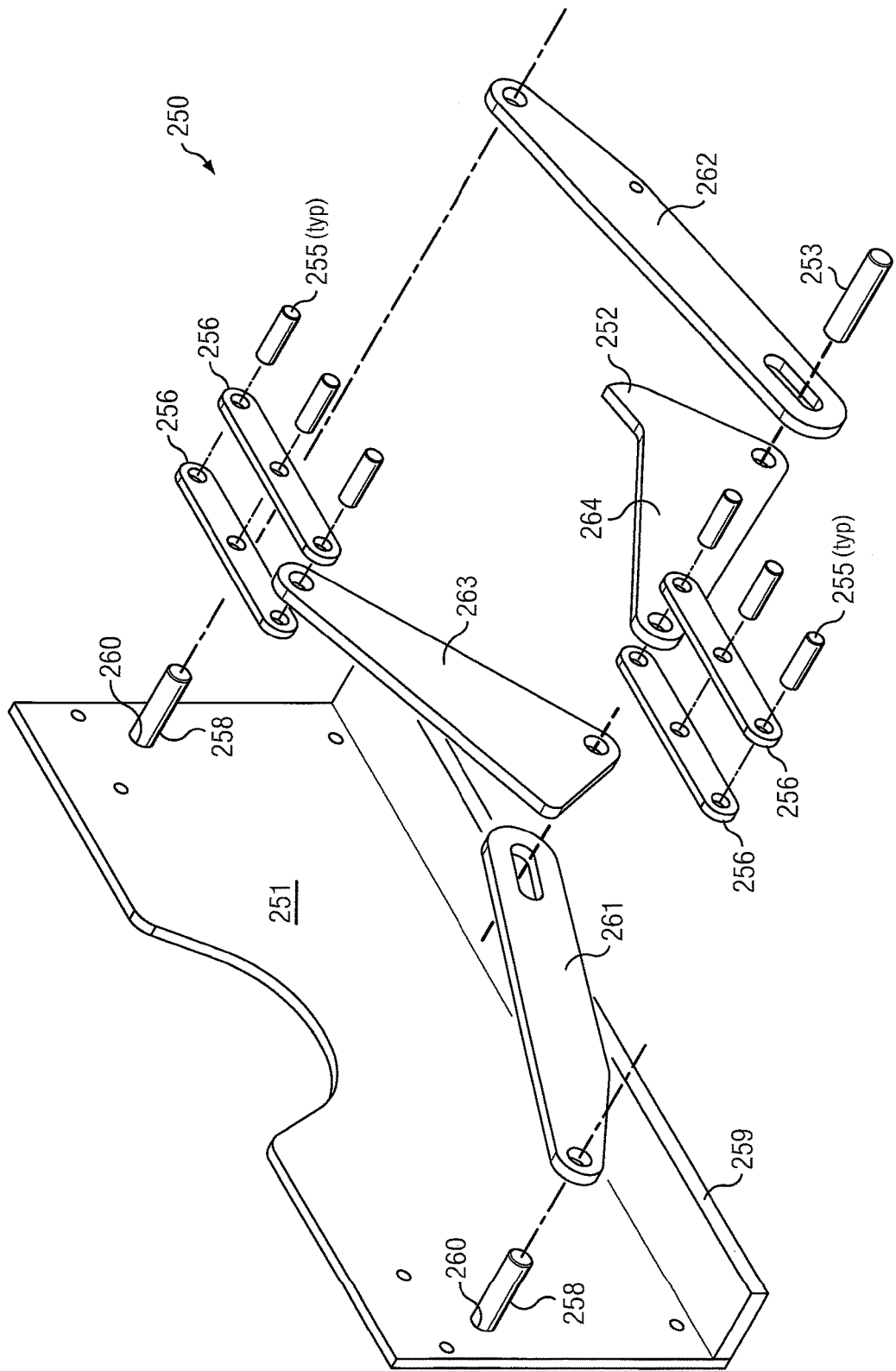

FIGS. 7A and 7B each illustrate one half of scissors mechanism 250 from FIG. 6, each in progressing stages of disassembly. For convenience on FIGS. 7A and 7B, the illustrated one-half of scissors mechanism 250 will be described with reference to FIGS. 7A and 7B as "scissors mechanism 250" even though, strictly speaking, it is one half thereof. FIG. 7A illustrates scissors mechanism 250 with one scissors end plate 251 pulled away, revealing the internal structure thereof. FIG. 7B illustrates such internal structure in an exploded view with one scissors end plate 251 and other parts omitted for clarity.

Referring first to FIG. 7A, it will be seen that first and second thrust arms 261 and 262, load up arm 263 and eject arm 264 all provided openings (holes or slots) in the proximal ends thereof to receive fulcrum pin 253. A lower end of each of scissors pistons 254 is rotatably anchored to scissor base 259, and an upper end of each is rotatably anchored to an assigned one of first and second thrust arms 261 and 262. The distal ends of first and second thrust arms 261 and 262 are each rotatably connected to rotation pins 258, which in turn are held in place in rotation pin holes 260 in scissor end plates 251. The distal ends of load-up arm 263 and eject arm 264 are each rotatably connected to the proximal end of an assigned pair of cantilever arms 256 via cantilever pins 255. A pair of cantilever arms 256 is provided on each side of scissors mechanism 250. Additional cantilever pins 255 hold cantilever arms 256 together through additional holes in cantilever arms 256. Cantilever pins 255, while holding cantilever arms 256 together, are further retained in slots between cantilever guides 257U and 257L. Nub 252 is provided on eject arm 264.

FIG. 7B illustrates the linkage of the moving parts in scissors mechanism with reference to an exploded view.

Returning to FIG. 7A, the operation of scissors mechanism 250 may be visualized. As noted before with reference to FIG. 3, the scissors mechanism as illustrated on FIG. 7A is in the "down" position. This refers to the position of fulcrum pin 253 when scissor pistons 254 are fully retracted. As scissor pistons 254 are extended, rotation of first and second thrust arms 261 and 262 about rotation pins 258 causes fulcrum pin 253 to elevate. As fulcrum pin 253 elevates, load up arm 263 and eject arm 264 also elevate, causing cantilever arms 256 to extend horizontally outwards, as guided by cantilever pins 255 retained between cantilever guides 257U and 257L. When scissor pistons 254 are fully extended, the fulcrum pin 253 (and the scissors mechanism 250) is in the "up" position, and cantilever arms 256 are fully extended horizontally outwards. As scissor pistons 254 retract again, the linkage of moving parts on FIG. 7A reverses, lowering fulcrum pin 253 (and the scissors mechanism 250) back to the "down" position, with cantilever arms 256 fully retracted horizontally inwards.

The application of the movement of scissors mechanism 250 between "up" and "down" positions to the handling of tubulars will be described in more detail below with reference to FIGS. 15A through 15G.

Figure 8:
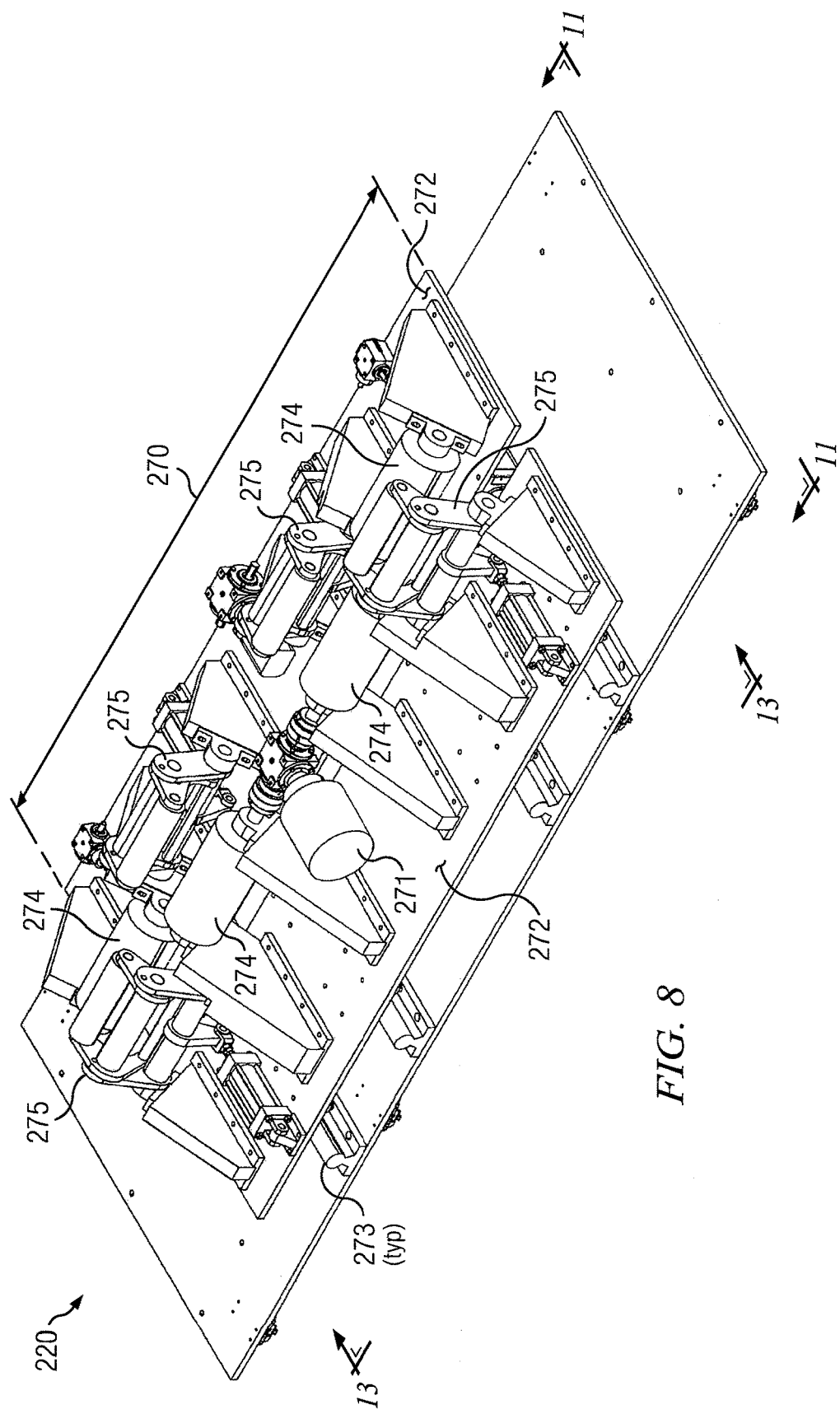
FIG. 8 is an illustration taken from FIG. 3, showing roller machine 270 on pod 220 in isolation.
Figure 9:
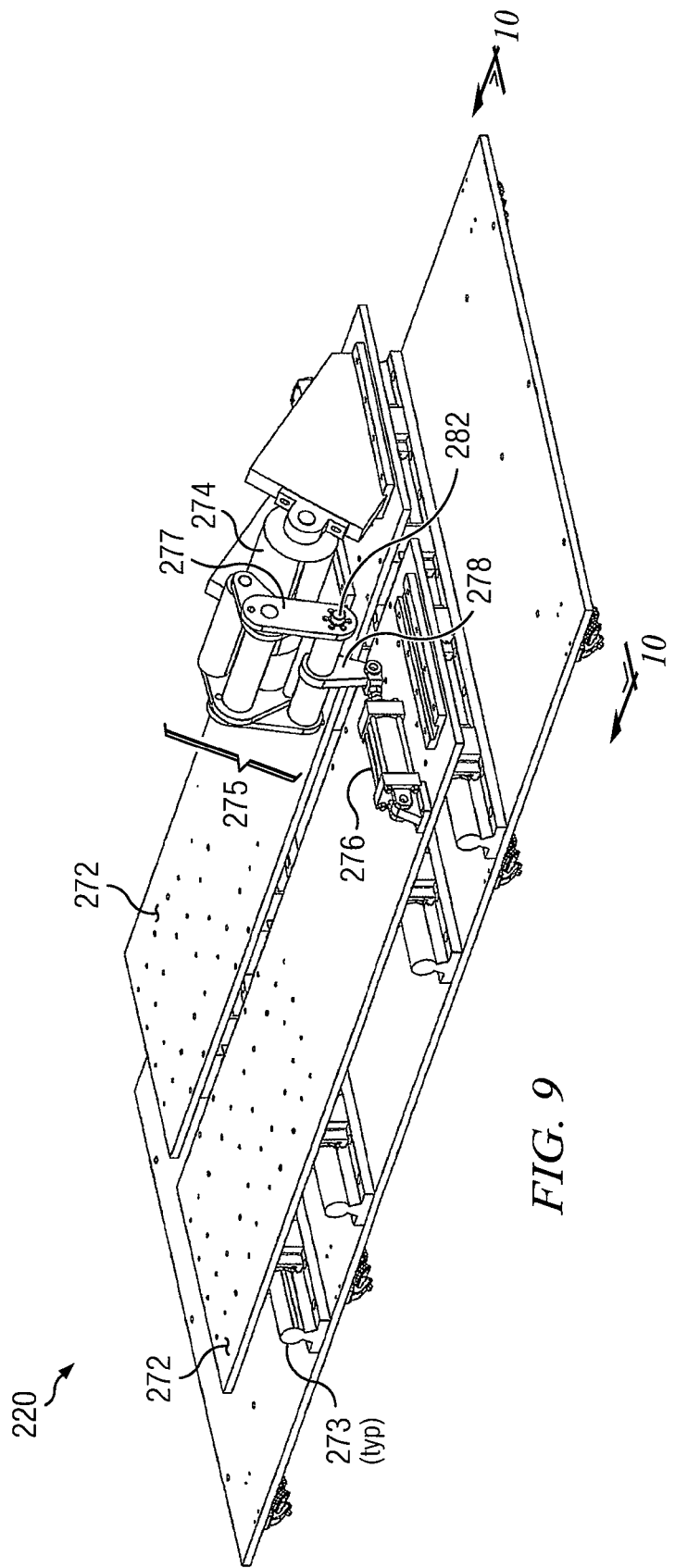
FIG. 9 illustrates, in isolation, one drive roller 274 opposing one pressure roller assembly 275.

FIG. 8 is an illustration taken from FIG. 3, showing roller machine 270 on pod 220 in isolation. Roller machine 270 on the embodiment of FIG. 8 comprises two mirror-image pairs of drive rollers 274 and pressure roller assemblies 275 either side of drive roller motor 271. Each pair comprises two (2) mirror-image sets, each set comprising one drive roller 274 opposing one pressure roller assembly 275, as shown in further isolation on FIG. 9. With further reference to FIGS. 8 and 9, opposing drive rollers 274 and pressure roller assemblies 275 are each anchored to corresponding one of opposing separation plates 272. Separation plates 272 are each deployed to displace laterally, independent of one another, by movement along plate rails 273.

With continuing reference to FIGS. 8 and 9, the independent displacement of separation plates 272 along plate rails 273 allows opposing drive rollers 274 and pressure roller assemblies 275 to be positioned at a user-selected distance apart, in order to accommodate a wide range of tubular diameters in roller machine 270. Although not illustrated on FIGS. 8 and 9, and to be described in more detail later with reference to additional Figures, user-selectable pressure rollers (having different pressure roller diameters) on pressure roller assemblies 275 further enable roller machine 270 to accommodate a wide range of tubular diameters.

The mechanism to position separation plates 272 may be one of several embodiments. Manual systems may allow free movement of separation plates by hand until in position, after which separation plates may be manually locked in position. In other embodiments, motor-driven worm gears or other actuating apparatus, running (for example) on teethed rails, may enable mechanically-controlled relative movement of separation plates until in position and locking down thereof. This disclosure is not limited to any type of mechanism to selectably position and lock separation plates 272.

Figure 10:
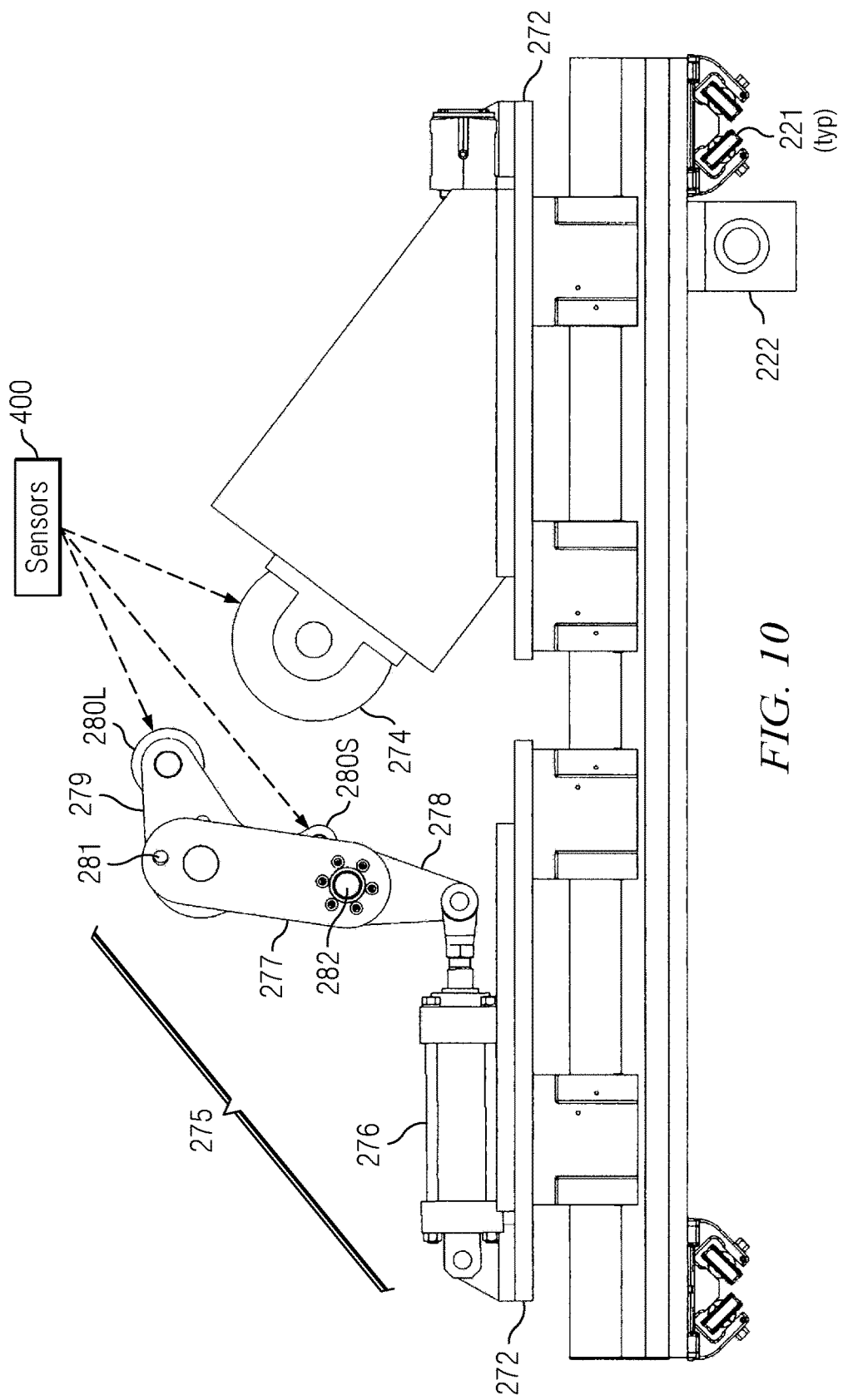
FIG. 10 is an elevation view of one set of an opposing drive roller 274 and pressure roller assembly 275 as shown on FIG. 9.

FIG. 10 is an elevation view of one set of an opposing drive roller 274 and pressure roller assembly 275 as shown on FIG. 9. Pressure roller assembly 275 on FIG. 10 comprises pressure roller piston 276 disposed, upon actuation thereof, to rotate pressure roller frame 277 via pressure roller arm 278. The linkage to enable this rotation is conventional, and an example thereof may seen by momentary reference to FIG. 9. Pressure roller piston 276 on FIG. 10 is in a fully retracted state. With reference to FIGS. 9 and 10 together, as pressure roller piston 276 is extended, pressure roller frame 277 lifts up and away from drive roller 274 via rotation about pressure roller pivot 282. Similarly, as pressure roller piston 276 is retracted, pressure roller frame moves down and towards drive roller 274, again via rotation about pressure roller pivot 282. This "up" and "down" movement of pressure roller frame 277 responsive to extension and retraction of pressure roller piston 276 will be seen in later Figures to allow tubulars to enter and exit roller machine 270 when pressure roller frame 277 is in the "up" position, and to cause pressure rollers to engage and hold tubulars to the drive rollers 274 when pressure roller frame 277 is in the "down" position.

FIG. 10 further illustrates large and small pressure rollers 280L and 280S at either end of boomerang arm 279. As will be described in further detail below with reference to FIGS. 12A and 12B, large and small pressure rollers 280L and 20S are user-selectable to engage a tubular according to the tubular's diameter. Users may select between large and small pressure rollers 280L and 280S via pin selector 281, as shown on FIG. 10. In the embodiment of FIG. 10, user selection via pin selector 281 is manual. Pin selector 281 is conventional. A pin may be manually withdrawn, freeing boomerang arm 279 to rotate on pressure roller frame 277, so as to enable manual selection between large and small pressure rollers 280L and 280S. Once selection is made, the pin is replaced into a locating hole on boomerang arm 279 corresponding to the selection, locking boomerang arm 279 in the selected position.

Figure 11:
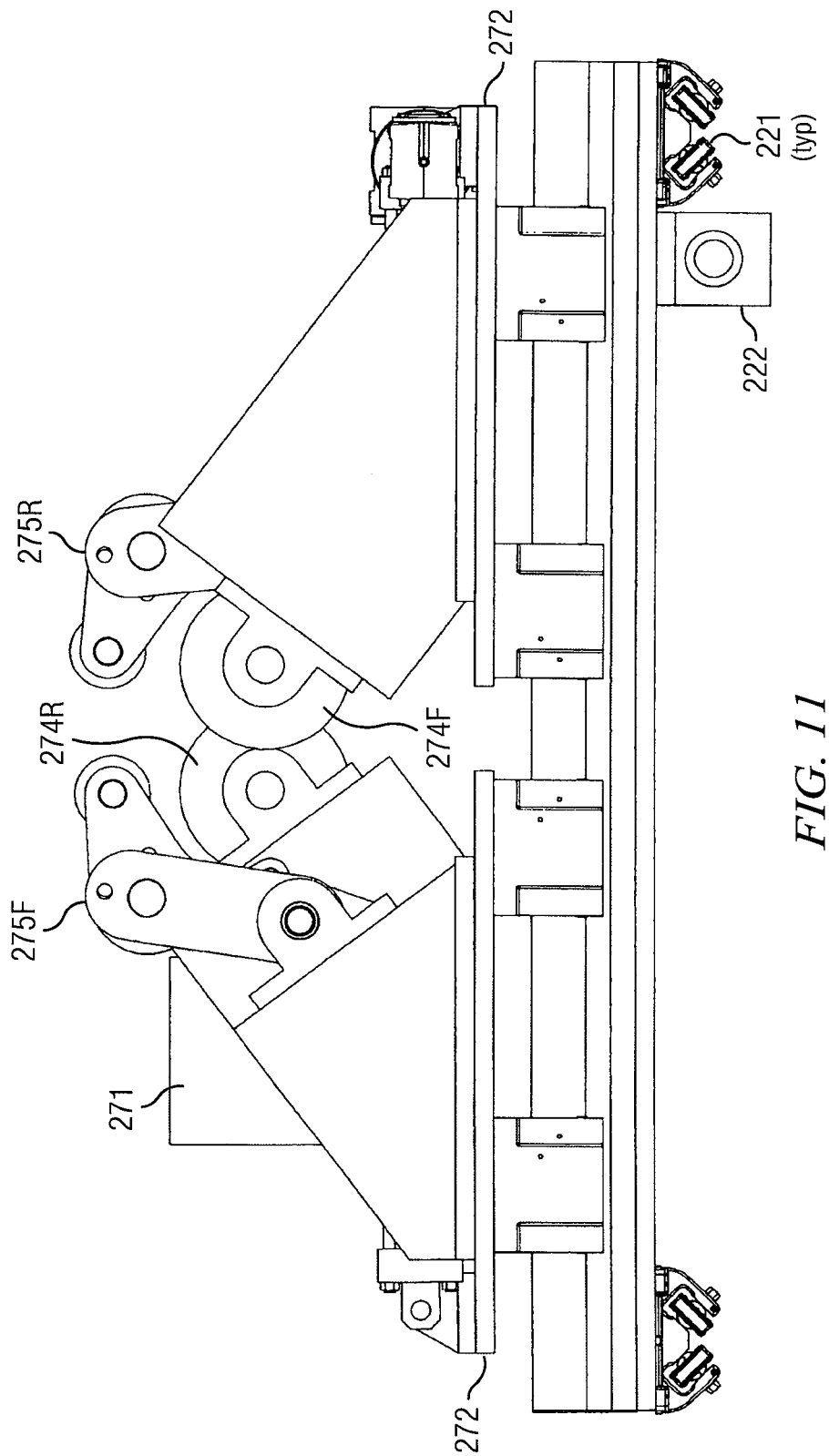
FIG. 11 is an elevation view as shown on FIG. 8.

FIG. 11 is an elevation view of two (2) sets of opposing drive rollers 274F and 274R, and pressure roller assemblies 275F and 275R, as shown on FIG. 8. On FIG. 11, drive roller 274F opposes pressure roller assembly 275F and is in the front of the illustration. Drive roller 274R opposes pressure roller assembly 275R and is in the rear of the illustration. From the point of view of an exemplary tubular engaged by drive rollers 274F and 274R, and pressure roller assemblies 275F and 275R (such an exemplary tubular not illustrated on FIG. 11), it will be seen that matched sets of opposing drive rollers and pressure roller assemblies, mirror-imaged with alternating orientation (as shown, for example, on FIG. 8), are able to fully cradle and retain tubulars in a wide range of diameters while rotating the tubulars at user-selectable speeds.

Figure 12A:
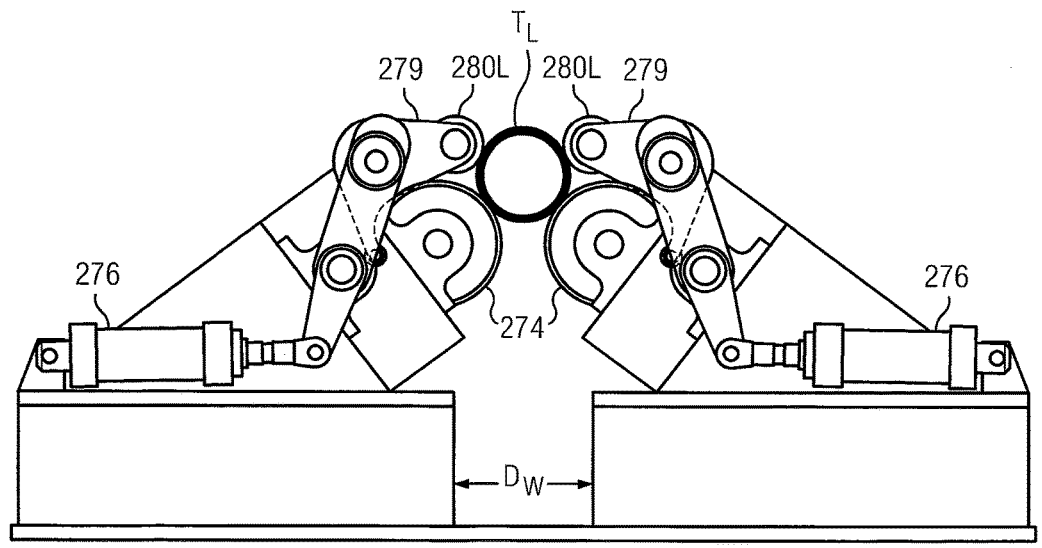
FIGS. 12A and 12B illustrate user selection between large and small pressure rollers 280L and 280S.
Figure 12B:
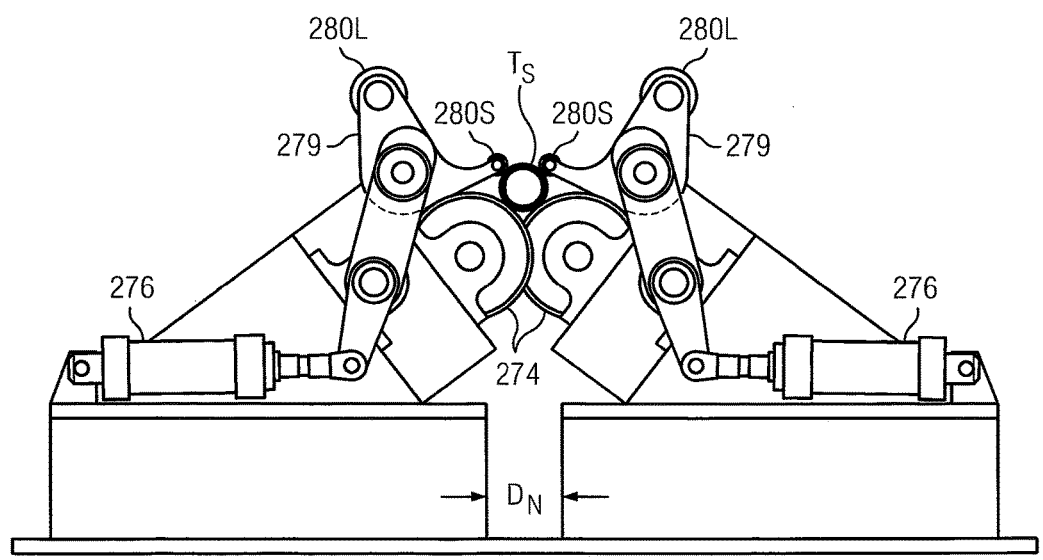

FIGS. 12A and 12B illustrate user selection between large and small pressure rollers 280L and 280S according to diameter of tubulars, as described more generally above with reference to FIG. 10. In FIG. 12A, a larger-diameter tubular $T_L$ is engaged by drive rollers 274 and large pressure rollers 280L. In FIG. 12B, and with reference to disclosure above associated with FIG. 10, boomerang arms 279 have been selectably repositioned to allow small pressure rollers 280S engage on a smaller-diameter tubular $T_S$.

FIGS. 12A and 12B further illustrate user selection of the separation between drive rollers 274 according to diameter of tubulars, as described more generally above with reference to the discussion of separation plates 272 in association with FIG. 8. FIG. 12A illustrates drive rollers 274 separated by a wider distance $D_W$ in order to accommodate a larger-diameter tubular $T_L$. FIG. 12B illustrates drive rollers 274 separated by a narrower distance $D_N$ in order to accommodate a larger-diameter tubular $T_S$.

FIG. 12B also illustrates, with further reference to FIG. 11 above, a further advantage of deploying matched sets of opposing drive rollers 274 and pressure roller assemblies 275, mirror-imaged with alternating orientation. FIG. 12B shows that opposing drive rollers 274 can effectively "overlap" to accommodate a smaller-diameter tubular $T_S$.

Figure 13:
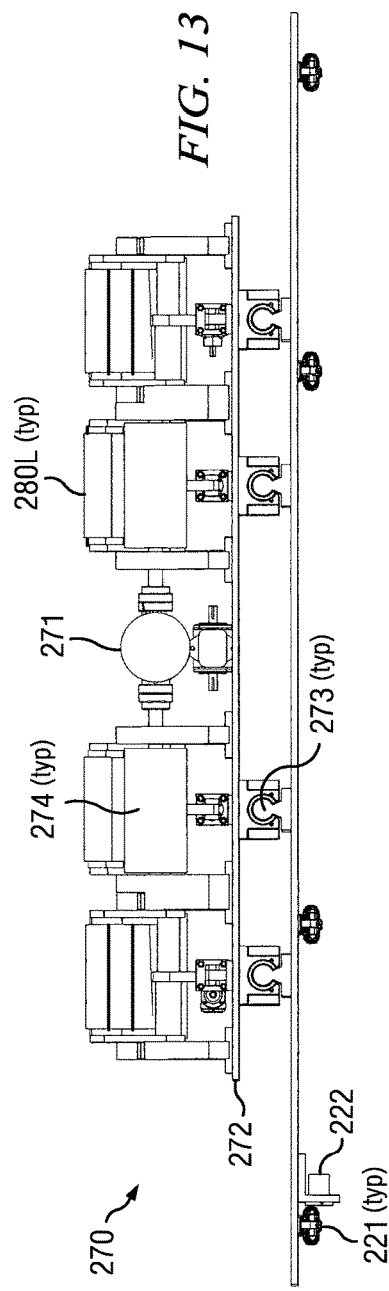
FIG. 13 is an elevation view of roller machine 270 as shown on FIG. 8.

FIG. 13 is an elevation view of roller machine 270 as shown on FIG. 8. FIG. 13 illustrates plate rails 273 enabling selectable separation of separation plates 272 as described above with reference to FIG. 8. FIG. 13 further illustrates pod wheels 221 and pod stop 222. As further described above with reference to FIG. 2, pods 220 travel on pod rails 203 to user-selectable positions according to the length of tubulars T on FIG. 2. Pod stop 222 ensures that pod 220 does not travel along pod rails 203 more than a pre-selected amount of travel FIG. 13 further illustrates drive roller motor 271, which is conventional. The PHS disclosed and illustrated herein is not limited by any type of drive roller motor 271, or linkage therefrom to rotate drive rollers 274 according to user-selectable speeds and/or directions.

Figure 14:
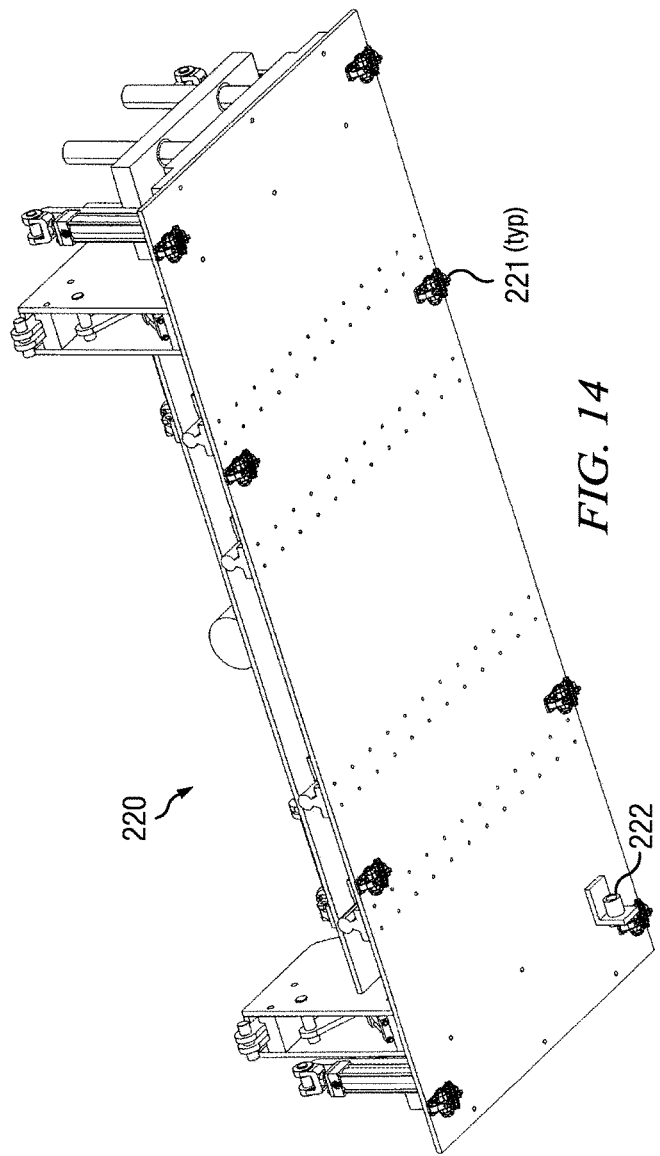
FIG. 14 is a view from underneath FIG. 3.

FIG. 14 is a view from underneath FIG. 3. Pod wheels 221 and pod stop 222 are shown consistent with related disclosure with reference to FIGS. 2 and 13.

FIGS. 15A through 15G are a series of "freeze frame" illustrations (sequentially in the form of a "movie") depicting the general operation of pods 220 consistent with PHS method 100 described generally above with reference to FIG. 1. In this way, FIGS. 15A through 15G collectively describe one embodiment of PHS 200 enabling PHS method 100 on FIG. 1. For reference, FIGS. 15A through 15G reflect a section through PHS 200 as shown on FIG. 2 as "FIG. 15".

Figure 15C:
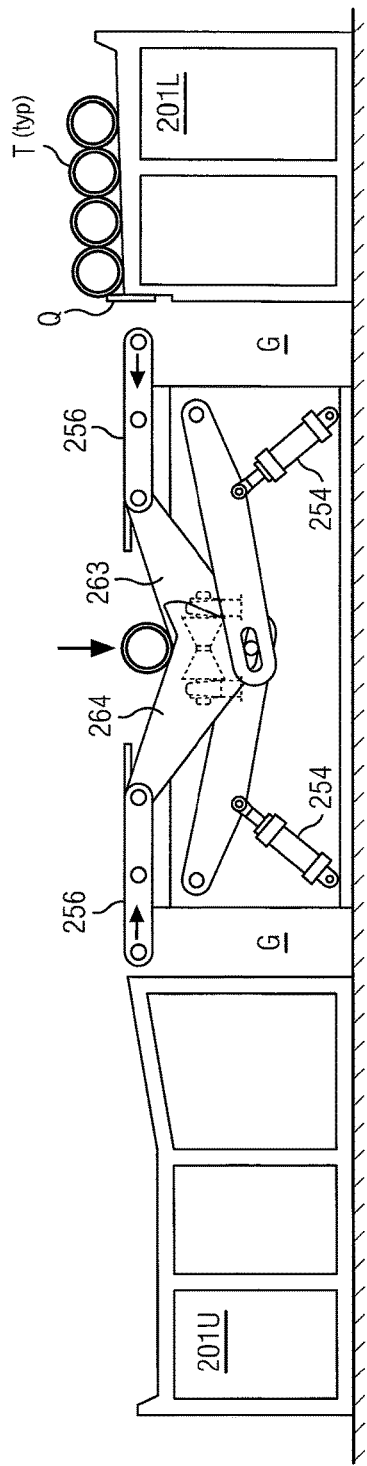

The following description of FIGS. 15A through 15G should be read in conjunction with related disclosure associated with FIGS. 2 through 11 above, and particularly with reference to FIG. 7A. In FIG. 15A, tubulars T are queued up on the load-side trestles 201L, and held in place by queuing regulator Q. Scissor pistons 254 are fully extended. Scissors mechanism 250 (from FIG. 7A) is in the "up" position and cantilever arms 256 are fully extended horizontally to bridge gaps G. FIG. 15A also shows a hidden view of index machine 230 (such hidden view labeled $230_H$). In $230_H$, index machine is close to being in its "up" position with index pistons 233 almost fully extended (from FIGS. 4 and 5).

In FIG. 15B, queuing regulator Q has been actuated to allow a tubular T to roll across cantilever arm 256 and load-up arm 263 until it comes to rest against nub 252.

In FIG. 15C, scissor pistons 254 are partially retracted, and scissors mechanism 250 (from FIG. 7A) is on its travel to the "down" position. Cantilevers 256 are retracting so as to open up gaps G. The tubular is being lowered, cradled temporarily by load-up arm 263 and eject arm 264.

Figure 15D:
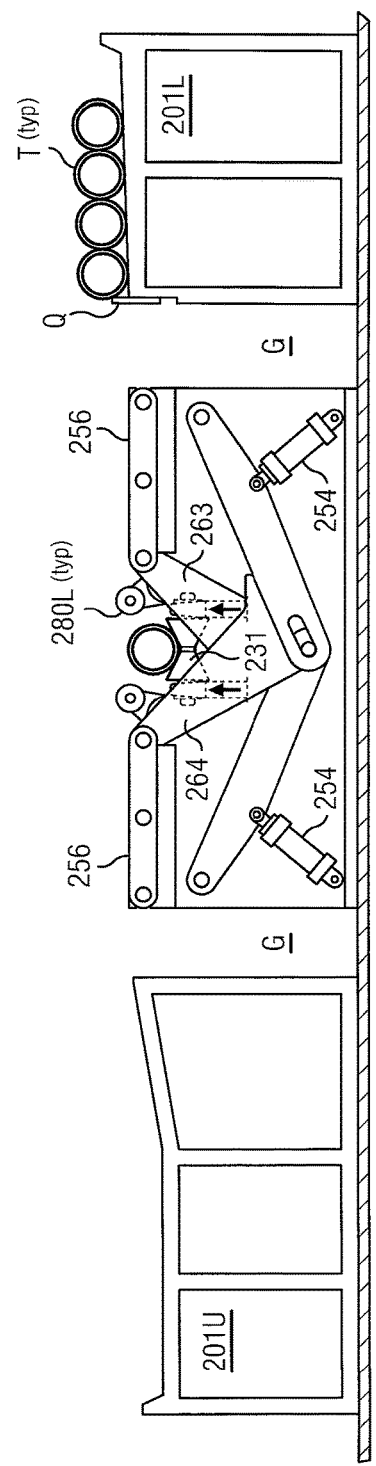

In FIG. 15D, scissor pistons 254 are fully retracted and scissors mechanism 250 (from FIG. 7A) is in its "down" position. Cantilever arms 256 are fully retracted and will permit ODS to pass unimpeded through gaps G, per FIG. 2 and associated disclosure. Index machine 230 (from FIGS. 4 and 5) has now been fully elevated to its "up" position. The full retraction of scissor pistons 254 causes load-up arm 263 and eject arm 264 to lower the tubular and rest it on index rollers 231. FIG. 15D also illustrates large pressure rollers 280L in the "up" position (from FIG. 10 and associated disclosure above).

Figure 15E:
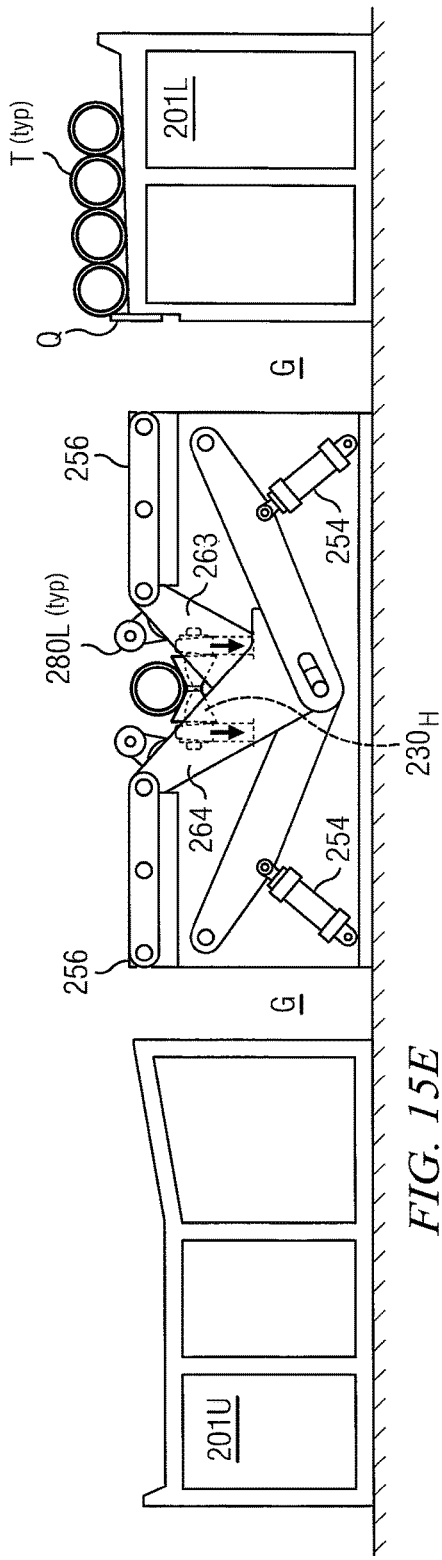

It will be appreciated that the tubular is indexed by index, machine 230 after FIG. 15D and before FIG. 15E. See disclosure associated with FIGS. 4 and 5 above for indexing.

Figure 15F:
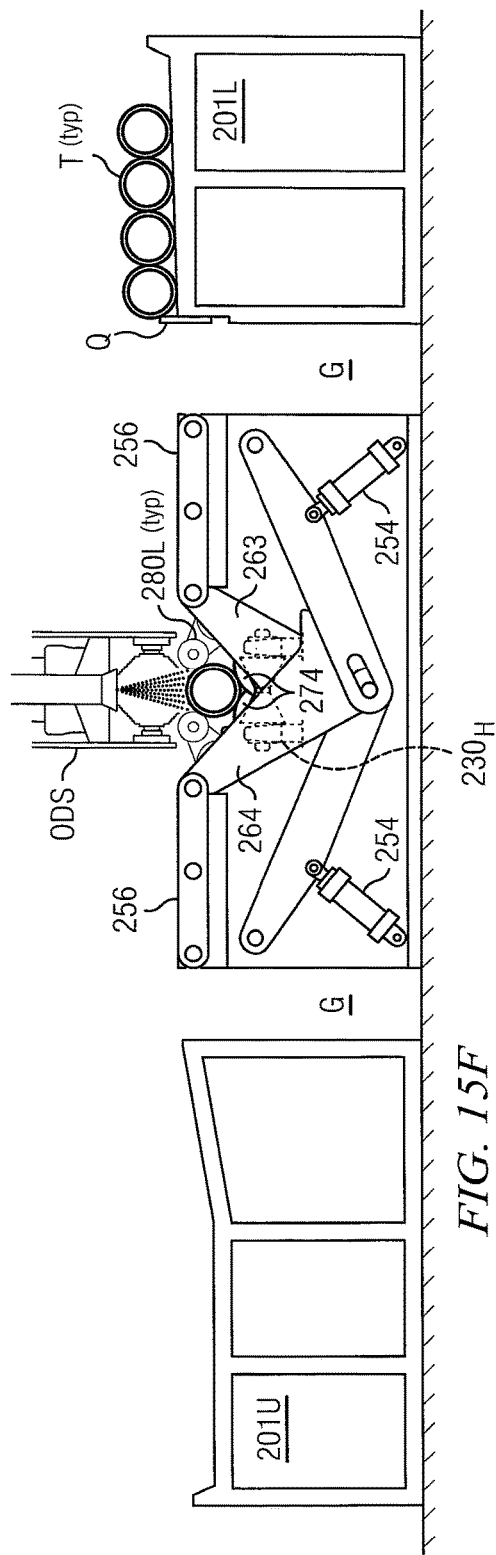

In FIGS. 15E and 15F, index machine lowers the tubular further by moving to its "down" position (by full retraction of index pistons 233 per FIGS. 4 and 5). Also in FIGS. 15E and 15F, on its way down to its "down" position, index machine 230 rests the tubular on drive rollers 274 on roller machine 270 (see FIGS. 8 through 11 and associated disclosure).

In FIG. 15F, the tubular is resting on drive rollers 274. Large pressure rollers 280L are retracted down towards their "down" position, per disclosure above associated with FIG. 10, until they contact the tubular on the upper side. The tubular may then be selectably rotated by drive rollers 274. The tubular is held in place and in pressure contact with driver rollers 274 during such rotation by large pressure rollers 280L. As further shown on FIG. 15F, ODS may perform cleaning, inspection and other operations on the rotating tubular. ODS may travel unimpeded on ODS rails 202 (see FIG. 2) along the full length of the tubular by passing through gaps G. It will be further appreciated from FIG. 15F that a top portion of the tubular is always in between and clear of pressure rollers 280L, enabling ODS to perform its operations on the full length of the tubular as it rotates.

Figure 15G:
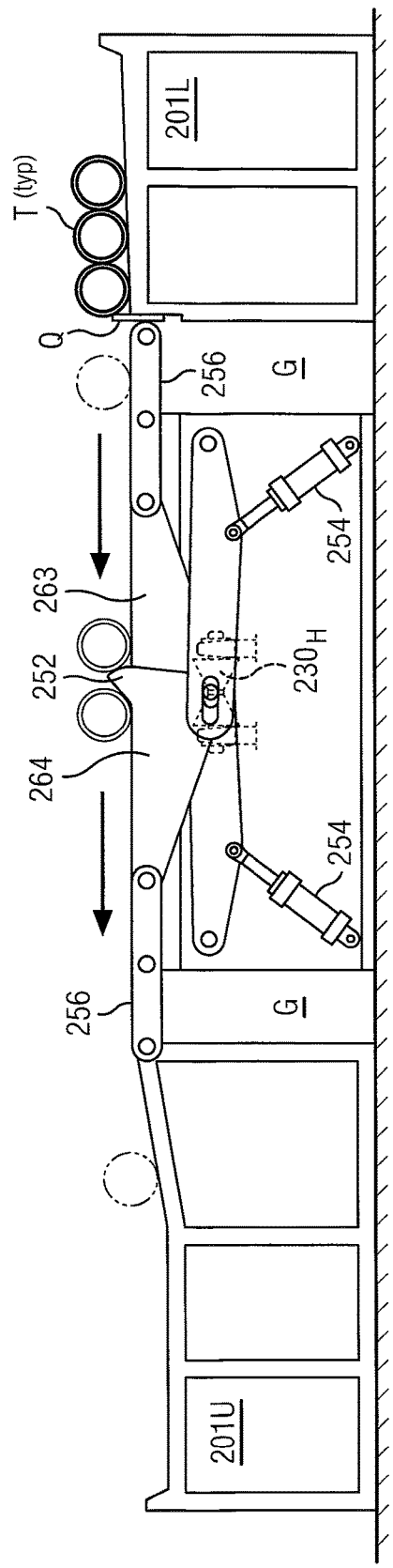

It will be appreciated that cleaning, inspection and other operations are performed on the tubular during FIG. 15F, but before FIG. 15G, until the tubular is deemed complete. In addition to the ODS operations described above with reference to FIG. 15F, MLI operations, Data Acquisition System (DAS) inspection operations, and other operations may be formed. See, for example, the disclosures of commonly assigned, co-pending U.S. patent application Ser. No. 14/040,650 (ODS), Ser. No. 13/832,340 (MLI) and Ser. No. 14/039,448 (DAS).

In FIG. 15G, operations on the tubular are complete. ODS is returned to its rest position, clear of PHS 200 (refer FIG. 2 and associated disclosure above). Pressure rollers 280L are brought up to their "up" position (refer FIG. 10 and associated disclosure above). The steps illustrated in FIGS. 15B through 15E are then essentially reversed. As illustrated on FIG. 15G, scissor pistons 254 extend to their fully-extended position, causing scissor mechanism 250 (from FIG. 7A) to elevate to its "up" position. On their way to the "up" position, load-up arm 263 and eject arm 264 cradle the tubular and pick the tubular up off drive rollers 274. Alternatively, load-up arm 263 and eject arm 264 pick the tubular off index rollers 231 if index rollers 231 have elevated and picked the tubular off drive rollers 274 first. Meanwhile, also on their way to the "up" position on scissor mechanism 250, cantilever arms 260 extend outwards again to bridge gaps G.

As the scissor mechanism 250 nears its "up" position, nub 252 contacts the tubular and causes the tubular to eject by rolling over eject arm 264, cantilever arm 256 on the unload side, and onto unload-side trestles 201U. Meanwhile, a new tubular is queued up from load-side trestles 201L, and is released by queue regulator Q no sooner than when the previous tubular is on its way to unload-side trestles 201U. The process returns to the sequence of events described above with reference to FIG. 15B.

It will be appreciated that sensors such as pressure sensors or accelerometers may be placed in various locations on PHS 200 in order to enhance control and safe operation of PHS 200. For example, as illustrated schematically on FIG. 10, sensors 400 (including pressure sensors and accelerometers) may be located in or around drive rollers 274 and pressure rollers 280L and 280S (disclosed with reference to FIGS. 8 through 11 above) in order to measure characteristics such as gravitational forces, torsional forces and vibration as the tubular rotates. The dotted lines on FIG. 10 illustrate such deployment of sensors 400 generally in or around drive rollers 274 and pressure rollers 280L and 280S. Data from sensors 400 may advantageously fed into a Data Acquisition System (DAS) such as is disclosed in commonly assigned, co-pending U.S. patent application Ser. No. 14/039,448. The DAS may then process the sensory data from PHS 200 in combination with other data acquired regarding cleaning, inspection and other operations while the tubular is being rotated.

In particular, without limiting the preceding paragraph, embodiments of PHS 200 will deploy sensors 400 as illustrated on FIG. 10 (including pressure sensors and accelerometers) in, on or around drive rollers 274 and pressure rollers 280L and 280S (disclosed with reference to FIGS. 8 through 11 above) to monitor vibrational response characteristics of the tubular during rotation at prescribed speeds. Data gathered during this process will then be used to characterize the tubular as "good" or "bad" based on comparison of the tubular's vibrational response characteristics with the vibrational response characteristics of similar tubulars compiled into historic baseline reference data. The acquired data during rotation at prescribed speeds is then compared by the DAS to such historic data to identify matches between compared specimens that predict a "good" or "bad" tubular, whose measured vibrational response characteristics are indicative of damage seen in historic reference specimens of similar tubulars.

Throughout this disclosure, reference has been made in preferred embodiments to components that are conventionally hydraulically-driven (such as pistons), or that are conventionally electrically-driven (such as motors). Such components are conventional. It will be further appreciated that the PHS as described in this disclosure is not limited to any particular method of actuating any of its specific moving parts. Substitutions may be made within the scope of this disclosure for suitable conventional enabling types of actuating mechanisms, including electrically-driven, hydraulically driven, pneumatically-driven, or otherwise.

Although the present invention and its advantages have been described in detail, it should be understood that various changes, substitutions and alternations can be made herein without departing from the spirit and scope of the invention as defined by the appended claims.

We claim:

1. A method for handling cylindrical tubulars in a handling machine, the handling machine comprising at least one pair of drive roller/pressure roller assemblies, the method comprising the steps of:
    (a) loading a first tubular onto the handling machine;
    (b) indexing the first tubular;
    (c) contacting the first tubular with the pair of drive roller/pressure roller assemblies, wherein each drive roller/pressure roller assembly includes at least one drive roller opposing at least one pressure roller, the assembly is configured to receive the first tubular between the drive roller and pressure roller, the pressure rollers are configured to be opened to allow the first tubular to enter and exit the handling machine, and in which step (c) includes contacting the first tubular with the drive rollers from underneath;
    (d) rotating the first tubular;
    (e) opening the pressure rollers;
    (f) ejecting the first tubular from the handling machine; and;
    (g) responsive to step (f), queuing a second tubular for entry into the handling machine, in which step (g) includes holding the second tubular out of the handling machine until the first tubular has completely vacated the handling machine;
    wherein the pressure rollers of the at least one pair of drive roller/pressure roller assemblies open to receive the first tubular in generally alternating orientations about a longitudinal axis of the first tubular.

2. The method of claim 1 in which step (c) includes the substep of contacting the first tubular with the drive rollers at azimuths of about 135 degrees and about 225 degrees where a circular cross-section of the first tubular is visualized with zero degrees pointing vertically upwards.

3. The method of claim 1 in which step (f) further comprises the substep of ejecting the first tubular laterally from the longitudinal axis of the first tabular.

4. The method of claim 1 in which step (f) further comprises the substep of ejecting the first tubular first tubular from the handling machine in a direction parallel with the longitudinal axis of the first tubular.

5. The method of claim 1 in which at least two of steps (a) through (g) are initiated manually at the selection of an operator.

6. The method of claim 1 in which:
    (1) step (a) includes the substep of manually initiating step (a) by an operator;
    (2) responsive to the manual initiation substep of step (a), subsequent selected steps are performed automatically, and (3) step (g) further includes waiting for further manual initiation from the operator before releasing the second tubular from the queuing.

7. The method of claim 1, further comprising:
(h) repeating steps (a) through (g) for a selected number of cycles.

8. The method of claim 1 in which step (b) further comprises the substep of indexing the first tubular to a pre-positioned indexing stop.

9. The method of claim 1 in which step (d) further comprises rotating the first tubular in a torsionally unrestrained environment.

10. The method of claim 1 in which the handling machine is movable, as a unit, from location to location.

11. The method of claim 1 in which at least one roller selected from the group consisting of the drive rollers and the pressure rollers on the handling machine includes at least one sensor selected from the group consisting of (1) a pressure sensor and (2) an accelerometer.

12. A method for handling cylindrical tubulars in a handling machine, the handling machine comprising at least one pair of drive roller/pressure roller assemblies, the method comprising the steps of:
(a) loading a first tubular onto the handling machine;
(b) indexing the first tubular;
(c) contacting the first tubular with the pair of drive roller/pressure roller assemblies, wherein each drive roller/pressure roller assembly includes at least one drive roller opposing at least one pressure roller, the assembly is configured to receive the first tubular between the drive roller and pressure roller, the pressure rollers are configured to be opened to allow the first tubular to enter and exit the handling machine, and in which step (c) includes contacting the first tubular with the drive rollers from underneath;
(d) rotating the first tubular;
(e) cleaning selected portions of the first tubular, wherein step (e) includes the substep of performing at least one cleaning operation selected from the group consisting of (1) jet cleaning and (2) brush cleaning;
(f) rotating the first tubular at different selected speeds during step (e);
(g) opening the pressure rollers;
(h) ejecting the first tubular from the handling machine; and;
(i) responsive to step (h), queuing a second tubular for entry into the handling machine, in which step (i) includes holding the second tubular out of the handling machine until the first tubular has completely vacated the handling machine;
wherein the pressure rollers of the at least one pair of drive roller/pressure roller assemblies open to receive the first tubular in generally alternating orientations about a longitudinal axis of the first tubular.

13. The method of claim 12 in which at least two of steps (a) through (i) are initiated manually at the selection of an operator.

14. The method of claim 12 in which:
(1) step (a) includes the substep of manually initiating step (a) by an operator;
(2) responsive to the manual initiation substep of step (a), subsequent selected steps are performed automatically, and
(3) step (i) further includes waiting for further manual initiation from the operator before releasing the second tubular from the queuing.

15. The method of claim 12, further comprising:
(k) repeating steps (a) through (i) for a selected number of cycles.

16. The method of claim 12 in which step (d) further comprises rotating the first tubular in a torsionally unrestrained environment.

17. The method of claim 12 in which at least one roller selected from the group consisting of the drive rollers and the pressure rollers on the handling machine includes at least one sensor selected from the group consisting of (1) a pressure sensor and (2) an accelerometer.

* * * * *